United States Patent
Voskuhl

(10) Patent No.: US 10,406,169 B2
(45) Date of Patent: *Sep. 10, 2019

(54) METHODS OF MONITORING ESTRIOL THERAPY

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/563,203

(22) PCT Filed: Mar. 29, 2016

(86) PCT No.: PCT/US2016/024754
§ 371 (c)(1),
(2) Date: Sep. 29, 2017

(87) PCT Pub. No.: WO2016/160832
PCT Pub. Date: Oct. 6, 2016

(65) Prior Publication Data
US 2018/0085379 A1    Mar. 29, 2018

Related U.S. Application Data

(60) Provisional application No. 62/140,239, filed on Mar. 30, 2015.

(51) Int. Cl.
| | | |
|---|---|---|
| *A61K 31/567* | (2006.01) | |
| *A61K 31/57* | (2006.01) | |
| *A61K 31/565* | (2006.01) | |
| *A61K 38/13* | (2006.01) | |
| *A61K 38/21* | (2006.01) | |
| *A61P 25/28* | (2006.01) | |

(52) U.S. Cl.
CPC .......... *A61K 31/567* (2013.01); *A61K 31/565* (2013.01); *A61K 31/57* (2013.01); *A61K 38/13* (2013.01); *A61K 38/21* (2013.01); *A61P 25/28* (2018.01); *A61K 2300/00* (2013.01)

(58) Field of Classification Search
CPC .... A61K 31/567; A61K 31/57; A61K 31/565; A61K 38/13; A61K 38/21
See application file for complete search history.

(56) References Cited

U.S. PATENT DOCUMENTS

| | | | |
|---|---|---|---|
| 3,932,635 A | 1/1976 | Segre | |
| 4,826,831 A | 5/1989 | Plunkett et al. | |
| 5,108,995 A | 4/1992 | Casper | |
| 9,962,395 B2 | 5/2018 | Voskuhl | |
| 2005/0113350 A1 | 5/2005 | Duesterberg et al. | |
| 2005/0239758 A1 | 10/2005 | Roby | |
| 2009/0005351 A1 | 1/2009 | Pickar et al. | |
| 2010/0168071 A1 | 7/2010 | Boissonneault | |
| 2013/0203722 A1 | 8/2013 | Voskuhl | |
| 2017/0049785 A1* | 2/2017 | Voskuhl | A61K 31/567 |
| 2017/0290845 A1* | 10/2017 | Voskuhl | A61K 31/565 |

FOREIGN PATENT DOCUMENTS

| | | |
|---|---|---|
| AU | 2004257772 A1 | 1/2005 |
| WO | WO-01070208 A2 | 9/2001 |
| WO | WO-2002/085374 | 10/2002 |
| WO | WO-2002/092102 A2 | 11/2002 |
| WO | WO-2002/092102 A3 | 11/2002 |
| WO | WO-2007/038435 A2 | 4/2007 |
| WO | WO-2007/038636 A2 | 4/2007 |
| WO | WO-2008/150547 A1 | 12/2008 |
| WO | WO-2010/050916 A1 | 5/2010 |
| WO | WO-2015/168000 A1 | 11/2015 |

OTHER PUBLICATIONS

Rubin, Susan; Parkinson's Disease in Women, 2015-2018, American Parkinson Disease Association, https:// www.apdaparkinson.org/parkinsons-disease-in-women/ (Year: 2015).*
Blasco et. al., Amyotrophic lateral sclerosis, 2012, Informa Healthcare, vol. 13, pp. 585-588 (Year: 2012).*
Chen et. al., Integrative Medicine International, 2014, Karger AG, vol. 1, pp. 223-225 (Year: 2014).*
Cubo et. al., Neurology, 2006, AAN Enterprises, vol. 67(7), pp. 1268-1271 (Year: 2006).*
Tiwari-Woodruff et. al., Journal of the Neurological Sciences, 2009, Elsevier, vol. 286, pp. 81-85 (Year: 2009).*
Anderson, "Adding estriol reduces ms relapse rate," Medscape Medical News, pp. 1-4 (2014). [https://www.medscape.com/viewarticle/824364].
Anonymous: "Estriol Treatment in Multiple Sclerosis (MS): Effect on Cognition," ClinicalTrials.gov archive, pp. 1-5 (2013). NCT01466114.
Extended European Search Report issued by the European Patent Office in corresponding Application No. EP 15786314.3, dated Dec. 1, 2017.
Extended European Search Report issued by the European Patent Office in corresponding Application No. EP 15786637.7, dated Dec. 1, 2017.
Kipp et al., "Multiple sclerosis: neuroprotective alliance of estrogen-progesterone and gender," Front Neuroendocrin, 33(1):1-16 (2012).
Soldan et al., "Immune modulation in multiple sclerosis patients treated with the pregnancy hormone estriol," J Immunol, 171(11):6267-6274 (2003).

(Continued)

*Primary Examiner* — Sarah Pihonak
(74) *Attorney, Agent, or Firm* — Foley Hoag LLP; David P. Halstead; Alexander J. Chatterley

(57) ABSTRACT

Provided are methods for treating a neurodegenerative disease, such as multiple sclerosis, in a subject receiving a first estriol treatment regimen, comprising obtaining a measurement of the serum estriol concentration in the blood of the subject, and administering a second estriol treatment regimen to the subject if the serum estriol concentration is less than 6 ng/mL. The daily amount of estriol administered during the second estriol treatment regimen is preferably greater than the daily amount of estriol administered during the first estriol treatment regimen.

17 Claims, 9 Drawing Sheets

(56) References Cited

OTHER PUBLICATIONS

Alhola et al., "Estrogen+ progestin therapy and cognition: A randomized placebo☐controlled double☐blind study," J Obstet Gynaecol Re, 36(4): 796-802 (2010).
Anderer et al., "Age-related cognitive decline in the menopause: effects of hormone replacement therapy on cognitive event-related potentials," Maturitas, 51(3): 254-269 (2005).
Gold et al., "Estrogen treatment in multiple sclerosis," J Neurol Sci, 286(1-2):99-103 (2009).
International Search Report of the International Searching Authority, dated Aug. 3, 2015, from related International Application No. PCT/US2015/027756.
International Search Report of the International Searching Authority, dated Aug. 5, 2015, from related International Application No. PCT/US2015/027752.
International Search Report of the International Searching Authority, dated Jan. 10, 2016, from related International Application No. PCT/US2015/047906.
International Search Report of the International Searching Authority, dated Jul. 11, 2016, from related International Application No. PCT/US2016/024754.
International Search Report of the International Searching Authority, dated Feb. 16, 2016, from related International Application No. PCT/US2015/056649.
International Search Report of the International Searching Authority, dated Jul. 21, 2016, from related International Application No. PCT/US2016/024751.
International Search Report of the International Searching Authority, dated Dec. 24, 2015, from related International Application No. PCT/US2015/052805.
Luchetti et al., "Gender Differences in Multiple Sclerosis: Induction of Estrogen Signaling in Male and Progesterone Signaling in Female Lesions," J Neuropathol Exp Neurol, 73(2): 123-135 (2014).
MacKenzie-Graham et al., "Estrogen treatment prevents gray matter atrophy in experimental autoimmune encephalomyelitis," J Neurosci Res, 90(7):1310-23 (2012).

Nicot, "Gender and sex hormones in multiple sclerosis pathology and therapy," Front Biosci (Landmark Ed), 14: 4477-4515 (2009).
Prempro and Premphase drug information, Food and Drug Administration, dated Jun. 5, 2003, Retrieved from the Internet. URL: http://www.fda.gov/ohrms/dockets/ac/03/briefing/3992B1_03_FDA-Prempro-Premphase.pdf.
Sicotte et al., "Treatment of Multiple Sclerosis with the Pregnancy Hormone Estriol," Ann Neurol, 52(4): 421-428 (2002).
Smith et al., "Impact of combined estradiol and norethindrone therapy on visuospatial working memory assessed by functional magnetic resonance imaging," J Clin Endocrinol Metab, 91(11):4476-81 (2006).
Speroff et al., "Postmenopausal hormone therapy," Gynecology and Obstetrics, Chapter 110, Mar. 8, 2011. URL: http://www.glowm.com/resources/glowm/cd/pp./v1/v1c110.html.
Extended European Search Report issued by the European Patent Office in corresponding Application No. 15846358.8, dated Apr. 17, 2018.
Holtorf et al., "The Bioidentical Hormone Debate: Are Bioidentical Hormones (Estradiol, Estriol, and Progesterone) Safer or More Efficacious than Commonly Used Synthetic Versions in Hormone Replacement Therapy?," Postgraduate Medicine, 121(1): 73-85 (2009).
Itoh et al., "Bedside to bench to bedside research: Estrogen receptor beta ligand as a candidate neuroprotective treatment for multiple sclerosis," J Neuroimmunol, 304:63-71 (2017).
Luine, "Estradiol and cognitive function: past, present and future," Horm Behav, 66(4):602-618 (2014).
Spence et al., "Neuroprotective effects of estrogens and androgens in CNS inflammation and neurodegeneration," Front Neuroendocrinol, 33(1):105-115 (2012).
Voskuhl et al., "Estriol combined with glatiramer acetate for women with relapsing-remitting multiple sclerosis: a randomised, placebo-controlled, phase 2 trial," Lancet Neurol, 15(1):35-46 (2016).
Zhang et al., "Distribution and differences of estrogen receptor beta immunoreactivity in the brain of adult male and female rats," Brain Res, 935(1-2):73-80 (2002).

* cited by examiner

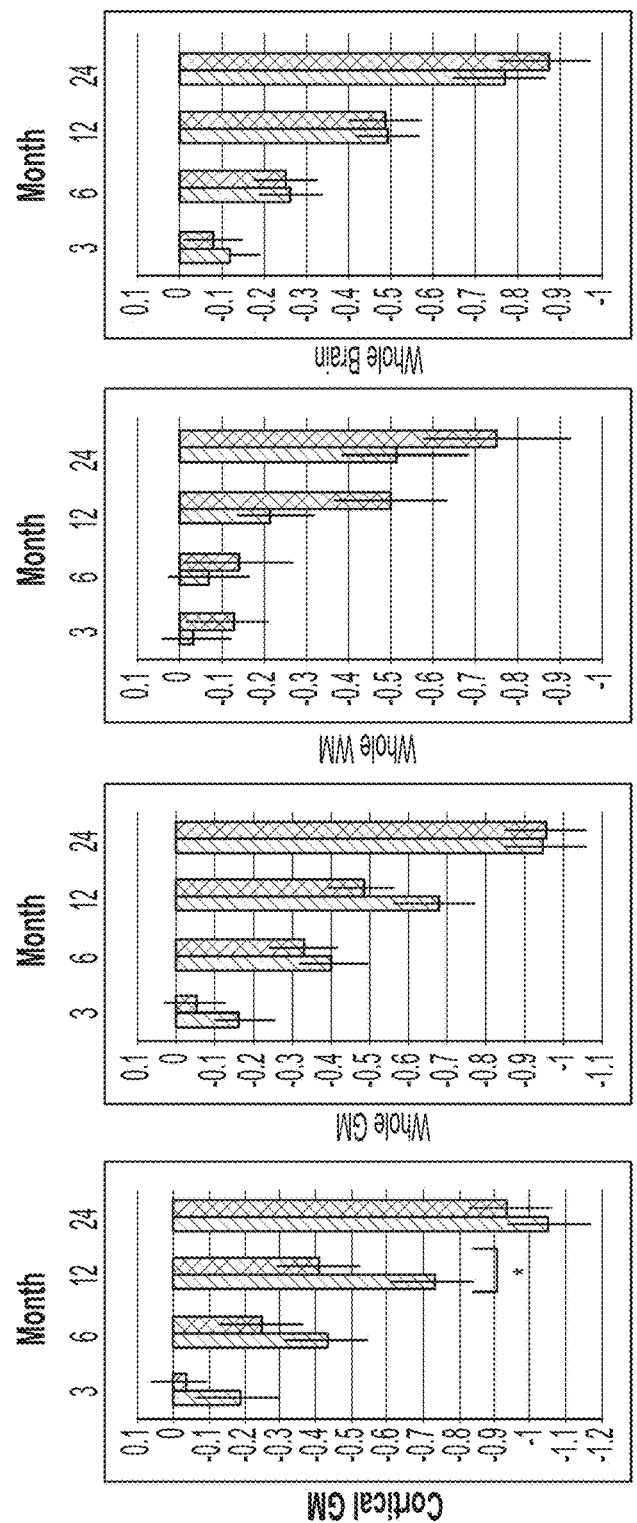

Placebo + GA

Estriol + GA

Placebo + GA vs. Estriol + GA

METHODS OF MONITORING ESTRIOL THERAPY

PRIORITY CLAIM

This application is a § 371 national-stage application based on PCT Application PCT/US16/024754, filed Mar. 29, 2016, which claims priority to U.S. Provisional Patent Application No. 62/140,239, filed Mar. 30, 2015, which is hereby incorporated by reference in its entirety.

BACKGROUND

Multiple sclerosis (MS) is a chronic, often debilitating disease affecting the central nervous system (brain and spinal cord). MS affects more than 1 million people worldwide and is the most common neurological disease among young adults, particularly women. The exact cause of MS is still unknown. MS is an autoimmune disease in which myelin sheaths surrounding neuronal axons are destroyed. This condition can cause weakness, impaired vision, loss of balance, and poor muscle coordination.

MS takes several forms, with new symptoms either occurring in isolated attacks (relapsing forms) or building up over time (progressive forms). Between attacks, symptoms may disappear completely; however, permanent neurological problems often occur, especially as the disease advances.

In 1996, the United States National Multiple Sclerosis Society described four clinical subtypes of MS: (i) relapsing-remitting; (ii) secondary-progressive; (iii) primary-progressive; and (iv) progressive-relapsing.

Relapsing-remitting MS is characterized by unpredictable relapses followed by periods of months to years of relative quiet (remission) with no new signs of disease activity. Deficits that occur during attacks may either resolve or leave sequelae, the latter in about 40% of attacks and being more common the longer a person has had the disease. This describes the initial course of 80% of individuals with MS. When deficits always resolve between attacks, this is sometimes referred to as benign MS, although people will still build up some degree of disability in the long term. On the other hand, the term malignant multiple sclerosis is used to describe people with MS having reached a significant level of disability in a short period of time. The relapsing-remitting subtype usually begins with a clinically isolated syndrome (CIS). In CIS, a person has an attack suggestive of demyelination but does not fulfill the criteria for multiple sclerosis; 30 to 70% of persons experiencing CIS go on to develop MS.

Secondary-progressive MS occurs in around 65% of those with initial relapsing-remitting MS, who eventually have progressive neurologic decline between acute attacks without any definite periods of remission. Occasional relapses and minor remissions may appear. The median length of time between disease onset and conversion from relapsing-remitting to secondary progressive MS is 19 years.

Primary-progressive MS occurs in approximately 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype, but similar to the age that secondary-progressive MS usually begins in relapsing-remitting MS, around 40 years of age.

Progressive-relapsing MS describes those individuals who, from onset, have a steady neurologic decline but also have clear superimposed attacks. This is the least common of all subtypes.

The following agents are approved by the U.S. Food and Drug Administration (FDA) to reduce disease activity and disease progression for many people with relapsing forms of MS, including relapsing-remitting MS, as well as secondary-progressive and progressive-relapsing MS in those people who continue to have relapses: dimethyl fumarate (Tecfidera®), fingolimod (Gilenya®), glatiramer acetate (Copaxone®), interferon beta-1a (Avonex® and Rebif®), interferon beta-1b (Betaseron® and Extavia®), peginterferon beta-1a (Plegridy®), mitoxantrone (Novantrone®), natalizumab (Tysabri®), alemtuzumab (Lemtrada®), and teriflunomide (Aubagio®). However, many of these therapies fail to successfully treat all patients or all symptoms in treated patients, and many of these therapies are associated with undesirable side effects. Accordingly, alternative therapies are needed.

SUMMARY

In some embodiments, the invention relates to a method for treating a neurodegenerative disease, such as multiple sclerosis, in a subject receiving a first estriol treatment regimen. The method may comprise obtaining a measurement of the serum estriol concentration in the blood of the subject, and administering a second estriol treatment regimen to the subject if the serum estriol concentration is less than a threshold value. The daily amount of estriol administered during the second estriol treatment regimen is preferably greater than the daily amount of estriol administered during the first estriol treatment regimen. The threshold value may be, for example, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, or 16 ng/mL.

Analogously, the method may comprise obtaining a measurement of the serum estriol concentration in the blood of the subject, and administering a third estriol treatment regimen to the subject if the serum estriol concentration is above a ceiling value. In this case, the daily amount of estriol administered during the third estriol treatment regimen is preferably lower than the daily amount of estriol administered during the first estriol treatment regimen. The ceiling value may be, for example, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, or 40 ng/mL.

The first treatment regimen, second treatment, and/or third treatment regimen may further comprise administering to the subject, for only a portion of each treatment period, a therapeutically effective amount of a progestogen, such as 0.7 mg of norethindrone daily.

BRIEF DESCRIPTION OF THE DRAWINGS

FIG. 1 includes two panels, identified as panels (A) and (B). Panel A shows the disposition of subjects enrolled in a clinical trial of estriol for treating multiple sclerosis. Panel B shows the study design. "Taper" indicates a period of reduction of either estriol or placebo over the course of 4 weeks at end of study, after month 24 clinic visit. Specifically, the dose of estriol was reduced by half (from 8 mg to 4 mg) for 2 weeks, then reduced by half again (from 4 mg to 2 mg) for 2 weeks, then discontinued. "x" indicates the administration of a progestin (0.7 mg norethindrone) orally each day for 2 weeks every three months, beginning at study month 6. "o" indicates the administration of a placebo for the progestin orally each day for 2 weeks every three months, beginning at study month 6.

FIG. 2 includes three panels, identified as panels (A), (B), and (C). Panel (A) shows that serum estriol concentrations are significantly increased at each time point after baseline (month 0) in the Estriol+GA group (-x-), while remaining below the assay detection limit in the Placebo+GA group (-). However, in the Estriol+GA group, estriol levels decreased by one-third at month 24 compared to month 3 (month 3 vs month 24, p=0.003; month 3 vs month 18, p=0.065). Estriol levels are expressed as mean+/−SE in ng/mL. Panel (B) shows the annualized confirmed relapse rates at months 0-12 and at months 0-24. Relapse rates decreased by 47% (p=0.021) in the Estriol+GA group compared to the Placebo+GA group at month 12 and decreased by 32% (p=0.098) at month 24. Panel (C) shows the proportion of subjects with confirmed relapses over 24 months, the between groups trend favored Estriol+GA (p=0.096).

FIG. 3 includes nine panels, identified as panels (A), (B), (C), (D), (E), (F), (G), (H), and (I). Panel (A) shows that EDSS improvement was observed at 24 months in the Estriol+GA within group comparison (median=−0.5, P=0.03), with no change in the Placebo+GA group (median=0, P=NS), and between groups comparison not reaching significance. (B) MFIS score improvement was observed at 24 months in the Estriol+GA within group comparison (median=−10.0, P=0.014), with no change in the Placebo+GA group (median=0, p=NS), and between groups comparison significant (P=0.03). (C) PASAT score improvement was observed at 12 months in the Estriol+GA within group comparison (P=0.005), with no change in the Placebo+GA group, and between group comparison significant (P=0.04), however scores assessed at the 24 month time point were no different between groups. All data are expressed as change in mean absolute scores over time as compared to baseline. (D-G) Change in volume from baseline for cortical gray matter in D; for whole gray matter in E; for whole white matter in F; and for whole brain in G. (H-I) Change in cortical gray matter (CGM), whole gray matter (GM) and whole white matter (WM) in subjects that were enhancing lesion positive in H, or enhancing lesion negative in I. Lower right: Significant voxel-wise gray matter loss from baseline to month 12 was more in Placebo+GA (top left subpanel) than in Estriol+GA (top right panel), with regions showing significant between group differences demonstrated by intensity heat map (bottom panel). Disabilities are expressed as means+/−SE. Negative values indicate improvement for EDSS and MFIS scores. Positive values indicate improvement for PASAT scores. EDSS=Expanded Disability Status Scale; MFIS=Modified Functional Impact Scale; PASAT=Paced Auditory Serial Addition Test (at 3 seconds). Volumes are expressed as mean percent change+/−SE from baseline. *=P<0.10, **=P<0.05. VBM results are visualized on the mean template and thresholded at P<0.05, FDR corrected. Black indicates Placebo+GA, while Gray indicates Estriol+GA.

FIG. 4 includes three panels, identified as panels (A), (B), and (C). Panel (A) shows MSQOL composite scores for Physical outcomes were improved in the Estriol+GA group (p=0.02), with no change in the Placebo+GA group, between group comparisons not reaching significance. Panel (B) shows MSQOL composite scores for Mental outcomes had trends similar to MSQOL Physical. Panel (C) shows Beck Depression Inventory (BDI) score improvement was observed at 24 months in the Estriol+GA group (median=−4.0, p=0.03), with no significant change in the Placebo+GA group (median=−3.5, p=NS), between groups not significant. All data are expressed as change in mean absolute scores over time as compared to baseline. Positive values indicate improvement for MSQOL Physical and Mental scores (panels (A) and (B)), while negative values indicate improvement for Depression scores (panel (C)).

FIG. 5 shows the percent change in PASAT scores at 12 months from baseline for all subjects (All, left bars), those with disability scores of less than 55 at baseline (<55, middle bars), and those with scores from 55 to the maximum of 60 at baseline (>55, right bars). A perfect PASAT score is 60, and scores lower than 55 depict disability. The data is expressed as mean % change+/−SE. **=P<0.05, *=P<0.10. The estriol group displayed a significant benefit as assessed by PASAT scores at P<0.10, and the subgroup of estriol subjects with PASAT scores less than 55 at baseline displayed a significant benefit at P<0.05.

FIG. 6 shows maximum intensity projections of voxel-wise gray matter atrophy superimposed onto 3 orthogonal planes through the brain. At 12 months, significant localized gray matter loss was observed in the Placebo+GA group as compared to baseline (top) and in the Estriol+GA group as compared to baseline (middle), each shown as gray against a black background in the 3 planes. Regions of significantly more gray matter loss in the Placebo+GA group as compared to the Estriol+GA group on between group comparisons are shown in white in the 3 planes (bottom). Gray matter loss is also visualized as projected onto a surface rendering of the mean template (lower right corner of each panel). All results are corrected for multiple comparisons by controlling the FDR at P≤0.05.

DETAILED DESCRIPTION

Figure 1A:
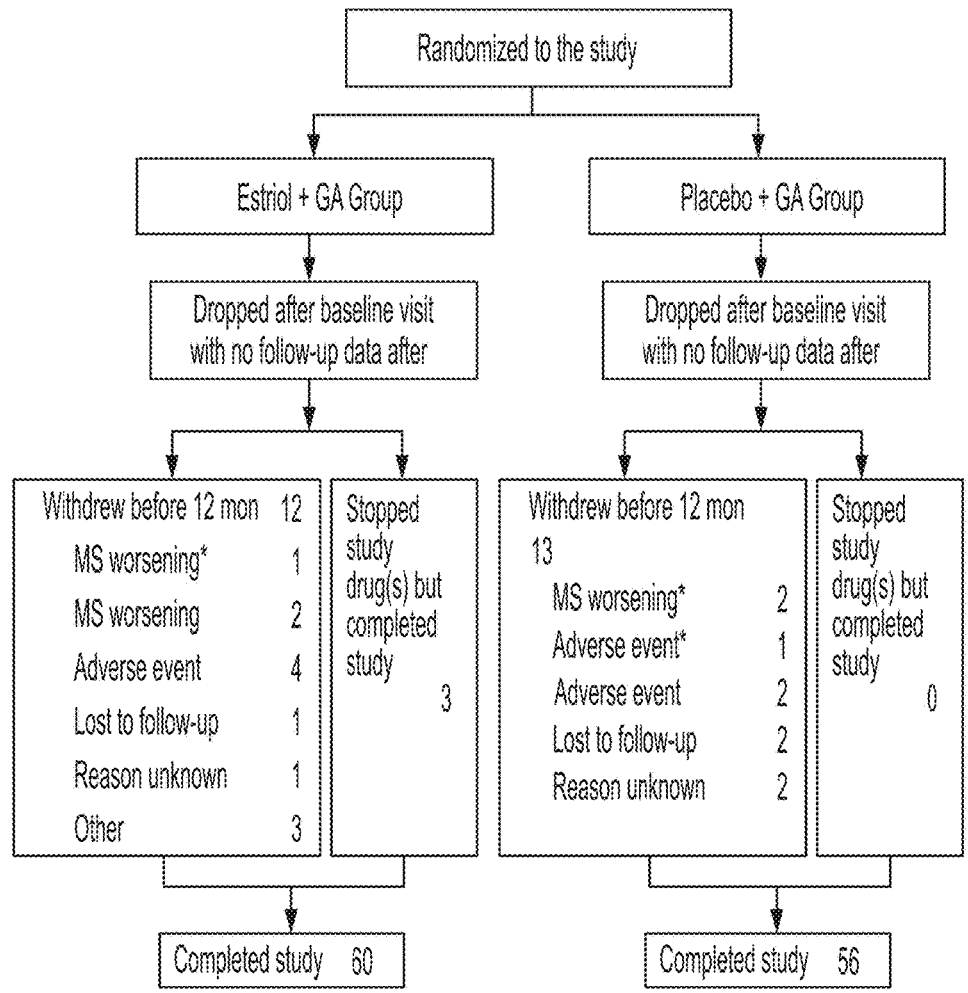
FIG. 1. Study overview.

As described herein, data obtained from clinical trials assessing the use of estriol in the treatment of multiple sclerosis demonstrates that patients who fail to maintain certain levels of estriol are less likely to benefit from certain therapeutic effects of estriol therapy than patients who maintain levels of estriol above that amount. Accordingly, assessing a patient's estriol level is a useful tool to ensure that that patient is receiving the appropriate therapeutic benefits, whether by increasing the dosage of estriol (e.g., to overcome some anomaly in the patient that causes standard doses of estriol to result in abnormally low levels of estriol in the bloodstream), or assisting the patient in complying with the therapeutic regimen (e.g., taking regular doses without skipping). Accordingly, some aspects of the invention relate to this finding that different serum estriol concentrations correlate with substantially different outcomes. Some aspects of the invention relate to the assessment or monitoring of serum estriol concentrations in patients receiving estriol therapeutics, e.g., to verify that the patient has achieved and/or is maintaining a level of estriol above a certain level or within a certain therapeutic window.

I. Administration of an Estriol

Some aspects of the invention are based on the finding that outcomes are better for patients receiving estriol therapy when serum estriol concentrations are maintained above a threshold value, below a ceiling value, or within an effective therapeutic window between a threshold value and a ceiling value. Accordingly, in some embodiments, the invention relates to a method for treating a neurodegenerative disease, such as multiple sclerosis, in a subject receiving a first estriol treatment regimen. The method may comprise obtaining a measurement of the serum estriol concentration in the blood of the subject, and administering a second estriol treatment regimen to the subject if the serum estriol concentration is less than a threshold value. The daily amount of estriol administered during the second estriol treatment regimen is preferably greater than the daily amount of estriol administered during the first estriol treatment regimen. The threshold value may be, for example, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, or 16 ng/mL.

In some embodiments, the invention relates to a method for treating a neurodegenerative disease, such as multiple sclerosis, in a subject receiving a first estriol treatment regimen. The method may comprise obtaining a measurement of the serum estriol concentration in the blood of the subject, and continuing the first estriol treatment regimen if the serum estriol concentration exceeds a threshold value. The threshold value may be, for example, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, or 16 ng/mL.

Analogously, the method may comprise obtaining a measurement of the serum estriol concentration in the blood of the subject, and administering a third estriol treatment regimen to the subject if the serum estriol concentration is above a ceiling value. In this case, the daily amount of estriol administered during the second estriol treatment regimen is preferably lower than the daily amount of estriol administered during the first estriol treatment regimen. The ceiling value may be, for example, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, or 40 ng/mL.

Similarly, the method may comprise obtaining a measurement of the serum estriol concentration in the blood of the subject, and continuing the first estriol treatment regimen if the serum estriol concentration is below a ceiling value. The ceiling value may be, for example, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, or 40 ng/mL.

In some embodiments, the invention relates to a method for treating a neurodegenerative disease, such as multiple sclerosis, in a subject. The method may comprise administering a first estriol treatment regimen to the subject, obtaining a measurement of the serum estriol concentration in the blood of the subject, and administering a second estriol treatment regimen to the subject if the serum estriol concentration is less than a threshold value. The daily amount of estriol administered during the second estriol treatment regimen is preferably greater than the daily amount of estriol administered during the first estriol treatment regimen. The threshold value may be, for example, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, or 16 ng/mL.

In some embodiments, the invention relates to a method for treating a neurodegenerative disease, such as multiple sclerosis, in a subject, comprising administering a first estriol treatment regimen to the subject, obtaining a measurement of the serum estriol concentration in the blood of the subject, and continuing the first estriol treatment regimen if the serum estriol concentration exceeds a threshold value. The threshold value may be, for example, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, or 16 ng/mL.

In some embodiments, the daily amount of estriol administered during the second estriol treatment regimen is less than the daily amount of estriol administered during the first estriol treatment regimen, for example, when the second estriol treatment regimen employs a different estriol formulation and/or route of administration, e.g., that increases the serum estriol concentration above the threshold value.

The method may comprise administering a first estriol treatment regimen to the subject, obtaining a measurement of the serum estriol concentration in the blood of the subject, and administering a third estriol treatment regimen to the subject if the serum estriol concentration exceeds a ceiling value. The daily amount of estriol administered during the third estriol treatment regimen is preferably less than the daily amount of estriol administered during the first estriol treatment regimen. The ceiling value may be, for example, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, or 40 ng/mL.

In some embodiments, the invention relates to a method for treating a neurodegenerative disease, such as multiple sclerosis, in a subject, comprising administering a first estriol treatment regimen to the subject, obtaining a measurement of the serum estriol concentration in the blood of the subject, and continuing the first estriol treatment regimen if the serum estriol concentration is less than a ceiling value. The ceiling value may be, for example, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, or 40 ng/mL.

In some embodiments, the method further comprises obtaining a second measurement of the serum estriol concentration in the blood of the subject (e.g., after at least a certain period of time, e.g., two months, three months, four months, five months, six months, nine months, one year, eighteen months, or two years) and administering a second estriol treatment regimen to the subject if the second measurement of the serum estriol concentration is less than a threshold value as defined herein. The method may comprise obtaining a second measurement of the serum estriol concentration in the blood of the subject and administering a third estriol treatment regimen to the subject if the second measurement of the serum estriol concentration is more than a ceiling value as defined herein.

In some embodiments, the method further comprises obtaining successive measurements of the serum estriol concentration in the blood of the subject and administering a second estriol treatment regimen to the subject if a measurement of the serum estriol concentration is less than a threshold value as defined herein. The method may comprise obtaining a successive measurement of the serum estriol concentration in the blood of the subject and administering a third estriol treatment regimen to the subject if a measurement of the serum estriol concentration is more than a ceiling value as defined herein. Measurements of the serum estriol concentration may be obtained, for example, once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. Measurements of the serum estriol concentration may be obtained once every 1, 2, 3, 4, 5, 6, 7, 8, 9, 10, 11, or 12 months. Measurements may be obtained once a year. Measurements of the serum estriol concentration may be obtained at least once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. Measurements of the serum estriol concentration may be obtained at least once every 1, 2, 3, 4, 5, 6, 7, 8, 9, 10, 11, or 12 months. Successive measurements of the serum estriol concentration may be obtained for at least 1 month, such as for at least 1, 2, 3, 4, 5, 6, 7, 8, 9, 10, 11, 12, 13, 14, 15, 16, 17, 18, 19, 20, 21, 22, 23, or 24 months, such as for at least 1, 2, 3, 4, 5, 6, 7, 8, 9, or 10 years. Successive measurements of the serum estriol concentration may be obtained for 1, 2, 3, 4, 5, 6, 7, 8, 9, 10, 11, 12, 13, 14, 15, 16, 17, 18, 19, 20, 21, 22, 23, or 24 months. Successive measurements of the serum estriol concentration may be obtained for 1, 2, 3, 4, 5, 6, 7, 8, 9, or 10 years.

In some embodiments, the method further comprises periodically obtaining a measurement of the serum estriol concentration in the blood of the subject and administering a second estriol treatment regimen to the subject if a measurement of the serum estriol concentration is less than a threshold value as defined herein. The method may comprise periodically obtaining a measurement of the serum estriol concentration in the blood of the subject and administering a third estriol treatment regimen to the subject if a measurement of the serum estriol concentration is more than a ceiling value as defined herein. Measurements of the serum estriol concentration may be obtained, for example, once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. Measurements of the serum estriol concentration may be obtained once every 1, 2, 3, 4, 5, 6, 7, 8, 9, 10, 11, or 12 months. Measurements may be obtained once a year. Measurements of the serum estriol concentration may be obtained at least once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. Measurements of the serum estriol concentration may be obtained at least once every 1, 2, 3, 4, 5, 6, 7, 8, 9, 10, 11, or 12 months. Measurements of the serum estriol concentration may be obtained periodically for at least 1 month, such as for at least 1, 2, 3, 4, 5, 6, 7, 8, 9, 10, 11, 12, 13, 14, 15, 16, 17, 18, 19, 20, 21, 22, 23, or 24 months, such as for at least 1, 2, 3, 4, 5, 6, 7, 8, 9, or 10 years. Measurements of the serum estriol concentration may be obtained periodically for 1, 2, 3, 4, 5, 6, 7, 8, 9, 10, 11, 12, 13, 14, 15, 16, 17, 18, 19, 20, 21, 22, 23, or 24 months. Measurements of the serum estriol concentration may be obtained periodically for 1, 2, 3, 4, 5, 6, 7, 8, 9, or 10 years.

In some embodiments, the daily amount of estriol administered during the third estriol treatment regimen is more than the daily amount of estriol administered during the first estriol treatment regimen, for example, when the third estriol treatment regimen employs a different estriol formulation and/or route of administration, e.g., that decreases the serum estriol concentration below the ceiling value.

The first treatment regimen may comprise, for example, administering orally to the subject, on a continuous basis for 84 consecutive days (12 weeks), 8 mg of estriol daily. The second treatment regimen may comprise administering orally to the subject, on a continuous basis for 84 consecutive days (12 weeks), 9 mg, 10 mg, 11 mg, 12 mg, 13 mg, 14 mg, 15 mg, or 16 mg of estriol daily. The third treatment regimen may comprise administering orally to the subject, on a continuous basis for 84 consecutive days (12 weeks), 0.5 mg, 1 mg, 2 mg, 3 mg, 4 mg, 5 mg, 6 mg, or 7 mg of estriol daily. The first treatment regimen, second treatment regimen, and/or third treatment regimen may comprise administering orally to the subject, for 14 consecutive days (2 weeks) of the 84 consecutive days (12 weeks), 0.7 mg of norethindrone daily. In some embodiments, the 14 consecutive days (2 weeks) of the 84 consecutive days (12 weeks) consist of the first 14 consecutive days (2 weeks) of the 84 consecutive days (12 weeks). Many variations of the first treatment regimen, second treatment regimen, and third treatment regimen fall within the scope of the invention as described infra.

The term estriol (E3) refers to estriol, esters thereof, and pharmaceutically acceptable salts of an ester thereof. For example, the estriol may be estriol, estriol succinate, estriol dihexanoate, or estriol sulfate. In certain embodiments, the estriol is formulated for oral administration.

In certain embodiments, the first treatment regimen comprises administering to the subject, on a continuous basis throughout one or more consecutive treatment periods, about 200 µg to about 20 mg of estriol daily, such as about 1 mg to about 10 mg of estriol daily, such as about 2 mg, about 3 mg, about 4 mg, about 5 mg, about 6 mg, about 7 mg, about 8 mg, about 9 mg, or about 10 mg of estriol daily. In certain embodiments, the first treatment regimen comprises administering to the subject, on a continuous basis throughout one or more consecutive treatment periods, a dose equal or equivalent to about 200 µg to about 20 mg of orally-administered estriol daily, such as about 1 mg to about 10 mg of orally-administered estriol daily, such as about 2 mg, about 3 mg, about 4 mg, about 5 mg, about 6 mg, about 7 mg, about 8 mg, about 9 mg, or about 10 mg of orally-administered estriol daily.

In certain embodiments, the second treatment regimen comprises administering to the subject, on a continuous basis throughout one or more consecutive treatment periods, about 1 mg to about 40 mg of estriol daily, such as about 2 mg to about 20 mg of estriol daily, such as about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of estriol daily. In certain embodiments, the second treatment regimen comprises administering to the subject, on a continuous basis throughout one or more consecutive treatment periods, a dose equal or equivalent to about 1 mg to about 40 mg of orally-administered estriol daily, such as about 2 mg to about 20 mg of orally-administered estriol daily, such as about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of orally-administered estriol daily.

In certain embodiments, the third treatment regimen comprises administering to the subject, on a continuous basis throughout one or more consecutive treatment periods, about 100 μg to about 10 mg of estriol daily, such as about 500 μg to about 8 mg of estriol daily, such as about 500 μg, about 1 mg, about 2 mg, about 3 mg, about 4 mg, about 5 mg, about 6 mg, about 7 mg, or about 8 mg of estriol daily. In certain embodiments, the third treatment regimen comprises administering to the subject, on a continuous basis throughout one or more consecutive treatment periods, a dose equal or equivalent to about 100 μg to about 10 mg of orally-administered estriol daily, such as about 500 μg to about 8 mg of orally-administered estriol daily, such as about 500 μg, about 1 mg, about 2 mg, about 3 mg, about 4 mg, about 5 mg, about 6 mg, about 7 mg, or about 8 mg of orally-administered estriol daily.

An "effective amount," as used herein, refers to an amount that is sufficient to achieve a desired biological effect. A "therapeutically effective amount," as used herein refers to an amount that is sufficient to achieve a desired therapeutic effect. For example, a therapeutically effective amount can refer to an amount that is sufficient to improve at least one sign or symptom of MS.

In some embodiments, a therapeutically effective amount of the estriol is sufficient to raise the serum estriol concentration above basal levels, and preferably to pregnancy levels or above pregnancy levels. In certain embodiments, a therapeutically effective amount of an estriol is selected to result in a serum estriol concentration in the blood of a patient equivalent to the serum estriol concentration in women in the second or third trimester of pregnancy. A therapeutically effective amount of estriol, for example, may be an amount of an estriol sufficient to increase the serum estriol concentration in the blood of a subject above a threshold value, such as 6 ng/mL. A therapeutically effective amount of an estriol may result in a serum estriol concentration of at least about 6 ng/ml, such as about 10 ng/ml to about 35 ng/ml, or about 20 ng/ml to 30 ng/ml (see generally Sicotte et al. *Neurology* 56:A75 (2001)). In some embodiments, a therapeutically effective amount of the estriol, for example, may be an amount of an estriol sufficient to increase the serum estriol concentration in the blood of a subject to a level above a threshold value but below a ceiling value (e.g., at least 6 ng/mL and not more than 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, or 40 ng/mL).

The dosage of the estriol may be selected for an individual patient depending upon the route of administration, severity of disease, age and weight of the patient, other medications the patient is taking and other factors normally considered by the attending physician, when determining the individual regimen and dosage level as the most appropriate for a particular patient. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected. In vitro or in vivo assays can be employed to help identify optimal dosage ranges.

The therapeutically effective dose of the estriol included in the dosage form is selected at least by considering the type of estriol selected and the mode of administration. The dosage form may include the estriol in combination with other inert ingredients, including adjuvants and pharmaceutically acceptable carriers for the facilitation of dosage to the patient as known to those skilled in the pharmaceutical arts. The dosage form may be any form suitable to cause the estriol to enter into the tissues of the patient.

Pharmaceutically acceptable carriers can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can include, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. Any agent described herein, if desired, can also comprise minor amounts of wetting or emulsifying agents, or pH buffering agents.

In one embodiment, the dosage form of the estriol is an oral preparation (liquid, tablet, capsule, caplet, or the like), which results in elevated serum estriol levels when consumed. The oral preparation may comprise conventional carriers including diluents, binders, time-release agents, lubricants, and disintegrants.

In some embodiments, the dosage form of the estrogen is a sublingual preparation, which results in elevated serum estrogen levels when consumed.

In some embodiments of the invention, the dosage form of the estriol may be provided in a topical preparation (lotion, cream, ointment, patch, or the like) for transdermal application.

Alternatively, the dosage form may be provided as a suppository or the like for transvaginal or transrectal application.

In some embodiments, the dosage form may also allow for preparations to be applied subcutaneously, intravenously, intramuscularly, or via the respiratory system.

II. Administration of a Progestogen

In preferred embodiments, the first treatment regimen, second treatment regimen, and/or third treatment regimen further comprises administering to the subject, for only a portion of each treatment period, a therapeutically effective amount of a progestogen.

The term "progestogen" (also known as "gestagen"), as used herein, refers to any steroid hormone that binds to and activates a progesterone receptor, or a precursor thereof. The term "progestogen" thus embraces naturally occurring, synthetic, and semi-synthetic forms of progestogen, and biologically active, pharmaceutically acceptable salts and esters thereof.

In certain embodiments, the progestogen is selected from chlormadinone acetate, cyproterone acetate, desogestrel, dienogest, 5α-dihydroprogesterone, drospirenone (Yasmin®), ethinodiol acetate, ethynodiol diacetate, etonogestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol, megestrol acetate (17α-acetoxy-6-dehydro-6-methylprogesterone), nestorone, nomegestrol acetate, norethindrone, norethindrone acetate (also known as norethisterone acetate), norethynodrel (Enovid®), norgestimate, norgestrel, progesterone, tanaproget, trimegestone, or a pharmaceutically acceptable salt of any of the foregoing, and any combination thereof.

In certain embodiments, progestogen is a progestin. The term "progestin" as used herein refers to a synthetic progestogen as defined herein. Examples of progestins include desogestrel, dienogest, drospirenone (Yasmin®), ethinodiol acetate, etonogestrel (Nexplanon®), gestodene, levonorgestrel (Alesse®), medroxyprogesterone acetate (Provera®), nestorone, nomegestrol acetate, norethindrone, norethindrone acetate, norethynodrel (Enovid®), norgestimate, norgestrel, and trimegestone.

In certain embodiments, the progestogen is selected from progesterone, 17-hydroxyprogesterone, 5α-dihydroprogesterone, norethindrone, norethindrone acetate (also known as norethisterone acetate), medroxyprogesterone acetate (17α-hydroxy-6α-methylprogesterone acetate), megestrol acetate (17α-acetoxy-6-dehydro-6-methylprogesterone), desogestrel, levonorgestrel, chlormadinone acetate, and cyproterone acetate, pharmaceutically acceptable salts of any of the foregoing, and any combination thereof. In certain embodiments, progestogen is selected from progesterone, 17-hydroxyprogesterone, 5α-dihydroprogesterone, norethindrone, norethindrone acetate (also known as norethisterone acetate), desogestrel, levonorgestrel, chlormadinone acetate, and cyproterone acetate, pharmaceutically acceptable salts and esters of any of the foregoing, and any combination thereof. In certain embodiments, progestogen is norethindrone or an ester thereof, or a pharmaceutically acceptable salt of an ester thereof, preferably norethindrone. In certain embodiments, progestogen is progesterone or an ester thereof, or a pharmaceutically acceptable salt of an ester thereof.

In certain embodiments, the progestogen is administered in a dose equal or equivalent to about 70 μg to about 7 mg norethindrone daily, such as about 100 μg to about 1 mg norethindrone daily, most preferably in a dose equal or equivalent to about 0.7 mg norethindrone daily. In certain preferred embodiments, the progestogen is norethindrone administered in a dose of 0.7 mg norethindrone daily.

In certain embodiments, the progestogen is formulated for oral administration, e.g., in a dose equal or equivalent to about 70 μg to about 7 mg norethindrone daily, such as about 100 μg to about 1 mg norethindrone daily, most preferably in a dose equal or equivalent to about 0.7 mg norethindrone daily. In certain preferred embodiments, the progestogen is norethindrone formulated for oral administration in a dose of 0.7 mg norethindrone daily.

In certain embodiments, the progestogen is orally administered in a dose equal or equivalent to about 70 μg to about 7 mg norethindrone daily, such as about 100 μg to about 1 mg norethindrone daily, most preferably in a dose equal or equivalent to about 0.7 mg (i.e., 700 μg) norethindrone daily. In certain preferred embodiments, the progestogen is norethindrone orally administered in a dose of 0.7 mg (i.e., 700 μg) norethindrone daily.

The therapeutically effective dose of the progestogen included in the dosage form can be selected at least by considering the type of progestogen selected and the mode of administration. The dosage form may include the progestogen in combination with other inert ingredients, including adjuvants and pharmaceutically acceptable carriers for the facilitation of dosage to the patient as known to those skilled in the pharmaceutical arts. The dosage form may be any form suitable to cause the progestogen to enter into the tissues of the patient.

In one embodiment, the dosage form of the progestogen is an oral preparation (liquid, tablet, capsule, caplet, or the like), which results in elevated serum progestogen levels when consumed. The oral preparation may comprise conventional carriers including diluents, binders, time-release agents, lubricants, and disintegrants.

In some embodiments of the invention, the dosage form of the progestogen may be provided in a topical preparation (lotion, cream, ointment, patch, or the like) for transdermal application.

Alternatively, the dosage form may be provided as a suppository or the like for transvaginal or transrectal application.

In some embodiments, the estriol and the progestogen are formulated together.

III. Treatment Periods

In some embodiments, the first treatment regimen, second treatment regimen, and/or third treatment regimen comprises administering the estriol to the subject on a continuous basis, e.g., for at least one treatment period, such as throughout two or more consecutive treatment periods. In certain embodiments, a continuous basis is daily, i.e., on consecutive days. For example, estriol administered (e.g., orally) to a subject on a daily basis throughout two or more consecutive treatment periods is deemed to be estriol administered to the subject on a continuous basis throughout two or more consecutive treatment periods. Similarly, estriol administered transdermally to a subject on a daily basis throughout two or more consecutive treatment periods is deemed to be estriol administered to the subject on a continuous basis throughout two or more consecutive treatment periods, such as 2, 3, 4, 5, 6, 7, 8, 9, 10, 11, 12, 13, 14, 15, 16, 17, 18, 19, 21, 22, 23, or 24 treatment periods.

As used herein, a "treatment period" refers to a period of time during which a subject is receiving, on a continuous or daily basis, at least one therapeutic agent administered for the purpose of treating a neurodegenerative disease in the subject. In certain embodiments, each treatment period in the first treatment regimen, second treatment regimen, and/or third treatment regimen is at least 28 consecutive days, at least 56 consecutive days, at least 84 consecutive days, at least 112 consecutive days, at least 140 consecutive days, or at least 168 consecutive days. For example, each treatment period may be 28, 29, 30, 31, 32, 33, 34, 35, 36, 37, 38, 39, 40, 41, 42, 43, 44, 45, 46, 47, 48, 49, 40, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 140, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 240, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 340, 351, 352, 353, 354, 355, 356, 357, 358, 359, 360, 361, 362, 363, 364, or 365 consecutive days.

In certain embodiments, each treatment period in the first treatment regimen, second treatment regimen, and/or third treatment regimen is at least 4 consecutive weeks, at least 8 consecutive weeks, at least 12 consecutive weeks, at least 16 consecutive weeks, at least 20 consecutive weeks, or at least 24 consecutive weeks. For example, each treatment period may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 consecutive weeks.

In certain embodiments, each treatment period in the first treatment regimen, second treatment regimen, and/or third treatment regimen is at least one month, at least two consecutive months, at least three consecutive months, at least four consecutive months, at least five consecutive months, or at least six consecutive months. For example, each treatment period may be 1, 2, 3, 4, 5, 6, 7, 8, 9, 10, 11, or 12 consecutive months.

The progestogen may be administered to the subject for only a portion of each treatment period, e.g., during the first treatment regimen, second treatment regimen, and/or third treatment regimen. As used herein, "for only a portion of each treatment period" refers generally to a period of time that occurs during but is at least one day shorter than a treatment period. In preferred embodiments, the phrase "for only a portion of each treatment period" refers generally to a period of consecutive days that occurs during but is at least one day shorter than a treatment period.

In certain embodiments, the portion of each treatment period in the first treatment regimen, second treatment regimen, and/or third treatment regimen is daily for all but at least 7 consecutive days of each treatment period. For example, if the treatment period is 28 days, the portion of such treatment period may be 1, 2, 3, 4, 5, 6, 7, 8, 9, 10, 11, 12, 13, 14, 15, 16, 17, 18, 19, 20, or 21 consecutive days. For convenience, such portion can begin on day 1 of a treatment period, such that, for this example, the portion can encompass day 1, days 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, or 1 to 21 of the treatment period.

In certain embodiments, the portion of each treatment period in the first treatment regimen, second treatment regimen, and/or third treatment regimen is daily for all but at least 14 consecutive days of each treatment period. For example, if the treatment period is 28 days, in various embodiments the portion of such treatment period may be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1, days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14 of the treatment period.

In certain embodiments, the portion of each treatment period in the first treatment regimen, second treatment regimen, and/or third treatment regimen is daily for up to 7 consecutive days of each treatment period. For example, if the treatment period is 28 days, in various embodiments the portion of such treatment period may be 1, 2, 3, 4, 5, 6, or 7 consecutive days. For convenience, such portion can begin on day 1 of a treatment period, such that, for this example, the portion can encompass day 1, days 1 to 2, 1 to 3, 1 to 4, 1 to 5, 1 to 6, or 1 to 7 of the treatment period.

In certain embodiments, the portion of each treatment period in the first treatment regimen, second treatment regimen, and/or third treatment regimen is daily for up to 14 consecutive days of each treatment period. For example, if the treatment period is 28 days, in various embodiments the portion of such treatment period may be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1, days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14 of the treatment period.

In certain embodiments, the portion of each treatment period in the first treatment regimen, second treatment regimen, and/or third treatment regimen is daily for all but at least half of each treatment period. For example, if the treatment period is 28 days, in various embodiments the portion of such treatment period may be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1, days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14 of the treatment period.

Preferably the progestogen is administered to the subject for only a portion of each treatment period in the first treatment regimen, second treatment regimen, and/or third treatment regimen. During the remainder of the treatment period for the first treatment regimen, second treatment regimen, and/or third treatment regimen, the subject may receive estriol but neither progestogen nor a placebo in place of the progestogen. Alternatively, during the remainder of the treatment period for the first treatment regimen, second treatment regimen, and/or third treatment regimen, the subject may receive both estriol and a placebo, e.g., in place of the progestogen.

IV. Subjects

The term "subject" as used herein refers to a living mammal and may be interchangeably used with the term "patient". In certain embodiments, the subject is a human. Preferably, a human subject is female, such as a woman. In certain embodiments, the subject is a premenopausal or perimenopausal woman. In certain embodiments, the subject is a premenopausal woman. In certain embodiments, the subject is a perimenopausal woman. In certain embodiments, the subject is a postmenopausal woman.

The subject may have multiple sclerosis. In certain embodiments, the multiple sclerosis is relapsing-remitting multiple sclerosis. In certain embodiments, the multiple sclerosis is secondary-progressive multiple sclerosis. In certain embodiments, the multiple sclerosis is primary-progressive multiple sclerosis. In certain embodiments, the multiple sclerosis is progressive-relapsing multiple sclerosis. In certain embodiments, the subject has a mild form of any one of the foregoing subtypes of MS. In certain embodiments, the subject has a moderate form of any one of the foregoing subtypes of MS. In certain embodiments, the subject has an aggressive form of any one of the foregoing subtypes of MS.

In certain embodiments, the multiple sclerosis is, more accurately, so-called clinically isolated syndrome (CIS). Estriol can be used, in accordance with the invention, to prevent or delay the onset of relapsing-remitting MS in subjects having CIS.

In some embodiments, the subject has radiologically isolated syndrome.

Although the methods disclosed throughout the specification and claims are useful for treating multiple sclerosis in its various forms and stages, these methods can also be applied the treatment of other neurodegenerative diseases, such as, by way of illustration, Alzheimer's disease, Parkinson's disease, stroke, amyotrophic lateral sclerosis, cerebellar ataxia, frontotemporal dementia, prion disease, Huntington's Disease, cerebral ischemia, idiopathic Morbus Parkinson, Parkinson syndrome, Morbus Alzheimers, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, degenerative retina disorders, trauma-induced brain damage, trauma-induced bone marrow damage, cerebral hyperexcitability symptoms, cerebral hyperexcitability states (e.g., of varying origin, such as after the addition of and/or withdrawal of medicaments, toxins, noxae and drugs), neurodegenerative syndromes of the peripheral nervous system, peripheral nerve injury, and spinal cord injury. In certain preferred embodiments, the neurodegenerative disease is multiple sclerosis.

V. Additional Therapeutic Agents

While the various methods disclosed herein are typically efficacious when administered without additional therapeutics, in certain embodiments, any of these methods may further comprise administering to the subject an immunotherapeutic agent, wherein the immunotherapeutic agent is neither an estriol nor a progestogen. That is, in certain embodiments the subject is administered, in addition to the estriol (and progestogen or placebo), a third agent useful in the treatment of neurodegenerative disease. Such agents useful in the treatment of MS are, in general, immunotherapeutic agents. At least in connection with MS, such agents are sometimes referred to as disease-modifying therapies or disease-modifying therapeutics (DMTs).

In certain embodiments, the method does not comprise administering an immunotherapeutic agent other than an estriol and a progestogen.

The term "immunotherapeutic agent" as used herein refers to a compound with an objectively measurable effect on at least one aspect of the immune system or an immune response. In certain embodiments, the immunotherapeutic agent is immunosuppressive, i.e., it exerts an objectively measurable inhibitory effect on at least one aspect of the immune system or an immune response. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is not an estriol. In certain embodiments, the immunotherapeutic agent is not a progestogen. Preferably, the immunotherapeutic agent is neither an estriol nor a progestogen.

In certain embodiments, the immunotherapeutic agent is selected from dimethyl fumarate (Tecfidera®), fingolimod (Gilenya®), glatiramer acetate (Copaxone®, for example "longer-lasting" 40 mg/ml or 20 mg/ml versions), interferon beta-1a (Avonex® or Rebif®), interferon beta-1b (Betaseron® or Extavia®), peginterferon beta-1a (Plegridy®), mitoxantrone (Novantrone®), natalizumab (Tysabri®), alemtuzumab (Lemtrada®), and teriflunomide (Aubagio®), mycophenolate mofetil, paclitaxel, cyclosporine, corticosteroids (e.g., prednisone, methylprenisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), peginterferon beta-1a (Plegridy®), mitoxantrone (Novantrone®), natalizumab (Tysabri®), alemtuzumab (Lemtrada®), and teriflunomide (Aubagio®).

In certain embodiments, the immunotherapeutic agent is dimethyl fumarate (Tecfidera®). In certain embodiments, the immunotherapeutic agent is fingolimod (Gilenya®). In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is peginterferon beta-1a (Plegridy®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is alemtuzumab (Lemtrada®). In certain embodiments, the immunotherapeutic agent is teriflunomide (Aubagio®).

In certain embodiments, the subject is already receiving a disease-modifying therapeutic. In this circumstance, the subject may continue to receive the disease-modifying therapeutic while taking the estriol (e.g., during a second treatment regimen or third treatment regimen), with and without the progestogen. Significantly, however, the dose of the disease-modifying therapeutic may be decreased when used in combination with the estriol, with and without the progestogen. For example, a current standard dose for glatiramer acetate (Copaxone®) is 40 mg subcutaneously (s.c.) three times a week, or 20 mg s.c. daily. In conjunction with estriol and progestogen in accordance with the invention, the dose for glatiramer acetate (Copaxone®) may be reduced by up to 50 percent or more, e.g., to 20 mg s.c. three times a week.

As another example, a current standard dose for fingolimod (Gilenya®) is 0.5 mg by mouth (p.o.) daily. In conjunction with estriol and progestogen in accordance with the invention, the dose for fingolimod (Gilenya®) may be reduced by up to 50 percent or more, e.g., to 0.25 mg p.o. daily.

As another example, a current standard dose for dimethyl fumarate (Tecfidera®) is 240 mg p.o. daily. In conjunction with estriol and progestogen in accordance with the invention, the dose for dimethyl fumarate (Tecfidera®) may be reduced by up to 50 percent or more, e.g., to 120 mg p.o. daily.

As yet another example, a current standard dose for interferon beta-1a (Avonex® or Rebif®) is 30 µg intramuscularly (i.m.) weekly (Avonex®) or 44 µg s.c. three days a week (Rebif®). In conjunction with estriol and progestogen in accordance with the invention, the dose for Avonex® may be reduced to 15 µg i.m. weekly, and the dose for Rebif® may be reduced to 22 µg s.c. three days a week.

As yet another example, a current standard dose for interferon beta-1b (Betaseron® or Extavia®) is 0.25 mg s.c. every other day (Betaseron® or Extavia®). In conjunction with estriol and progestogen in accordance with the invention, the dose for interferon beta-1b (Betaseron® or Extavia®) may be reduced to 0.125 mg s.c. every other day.

In certain embodiments, the subject is receiving an immunotherapeutic agent and has cognitive disability. For example, if a subject scores below 50 on PASAT, and optionally if such low score is verified upon retest within about one week to one month, then the subject may be deemed to have cognitive disability. In accordance with the invention, this cognitive disability is treated with estriol, and, in certain embodiments, followed up with further retest e.g., about six months from the start of a second treatment regimen or third treatment regimen, such as to achieve an increase in test score of at least 3 points.

In certain embodiments, the subject is receiving an immunotherapeutic agent and has progressive walking disability. For example, the subject performs a 25 foot walk test, e.g., at 0 months (baseline), 6 months, 1 year, and/or 2 years. If there is documented worsening in walking (takes more seconds), e.g., by 20 percent as compared to baseline, and this worsening is confirmed on a repeated walk test, e.g., about 3 months later, then the subject is deemed to have progressive worsening in walking. In accordance with the invention, this progressive walking disability is treated with estriol, and, in certain embodiments, followed up with repeat walking test, e.g., at about 1 year or 2 years from the start of a second treatment regimen or third treatment regimen, such as to stabilize or halt any further worsening in walking times.

In certain embodiments, the subject is receiving an immunotherapeutic agent and experiencing a relapse or progression of the multiple sclerosis. For example, a subject may experience a relapse or progression while on a maintenance dose of a DMT. Such subject can then begin concurrent treatment with estriol in accordance with any of the various methods disclosed herein, e.g., to reduce the frequency and/or severity of relapses or to slow progression of the disease (e.g., as determined by assessment of one or more of walking, vision, balance, cognition, or other symptoms of the condition, e.g., as measured according to the Expanded Disability Severity Scale (EDSS) and/or the multiple sclerosis functional composite (MSFC)). Thus, the various embodiments of the methods disclosed herein can be methods for improving walking, vision, balance, cognition, or other symptoms in a subject, such as a subject with multiple sclerosis, and/or methods for improving EDSS or MSFC scores in a subject, such as a subject with multiple sclerosis.

In certain embodiments, the subject is receiving an immunotherapeutic agent and experiencing a relapse of the multiple sclerosis. For example, a subject may experience a relapse while on a maintenance dose of a DMT. Such subject can then begin concurrent treatment with estriol in accordance with a method of the present invention, e.g., to reduce the frequency and/or severity of relapses.

In certain embodiments, the subject is receiving an immunotherapeutic agent selected from interferon-beta 1a, interferon-beta 1b, peginterferon beta-1a, glatiramer acetate, natalizumab, alemtuzumab, mitoxantrone, fingolimod, teriflunomide, and dimethyl fumarate during a ramp-up period for dose of the immunotherapeutic agent, e.g., the patient begins receiving the immunotherapeutic and the estriol therapy at the same time or at about the same time (such as for patients who have not previously received treatments for their disease). Advantageously, estriol induces a rapid onset of therapeutic effect on MS, while commonly an immunotherapeutic agent such as interferon-beta 1a, interferon-beta 1b, peginterferon beta-1a, glatiramer acetate, natalizumab, alemtuzumab, mitoxantrone, fingolimod, teriflunomide, or dimethyl fumarate may take weeks to months to induce observable improvements on some or all symptoms.

In certain embodiments, the subject is receiving glatiramer acetate during a ramp-up period for dose of the glatiramer acetate. In other certain embodiments, the subject is not already receiving a disease-modifying therapeutic.

VI. Formulations

In certain embodiments, the estriol and the progestogen are formulated separately from one another, e.g., the subject receives the estriol as a single formulation and the progestogen as a separate formulation. For oral administration, a given dose of each formulation may comprise one or more pills, tablets, capsules, or the like (i.e., unit doses). For example, an 12 mg dose of estriol can be administered as six 2 mg capsules, and a 0.7 mg dose of norethindrone can be administered as a single capsule, though preferably each dose is administered in a single unit dose (e.g., one unit dose each for the estriol and the progestogen).

In certain embodiments, e.g., where a placebo is administered with the estriol on days when progestogen is not administered, the estriol and the placebo are formulated separately from one another. For example, the subject is administered the estriol as a single formulation and the placebo as a separate formulation. For oral administration, a given dose of each formulation can comprise one or more pills, tablets, capsules, or the like (i.e., unit doses). For example, an 12 mg dose of estriol can be administered as six 2 mg capsules, and a placebo can be administered as a single capsule.

When a given dose of any agent involves administration of more than a single unit dose, e.g., six 2 mg capsules of estriol, the individual unit doses can be administered at essentially the same time, or they can be administered at different times on a given day, provided the entire daily dose is administered within a single day. For example, six 2 mg capsules of estriol can be taken together essentially once a day, or they may be taken three at a time twice a day, or they may be taken two at a time three times a day. Additional schedules are contemplated by the invention, again provided the entire daily dose is administered within a single day. While it may be preferable that the subject follow the same schedule from one day to the next, such is not required, once again provided the entire daily dose is administered within a single day.

When the estriol and the progestogen are formulated separately, they can be administered essentially simultaneously, or they can be administered sequentially with respect to each other. For example, in one embodiment the subject is administered six 2 mg capsules of estriol and one 0.7 mg capsule of norethindrone essentially simultaneously. In an embodiment, the subject is administered estriol in divided doses, e.g., three 2 mg capsules twice daily, and the progestogen is administered essentially simultaneously with one of the divided doses of estriol. In yet another embodiment, the subject is administered estriol in divided doses, e.g., three 2 mg capsules twice daily, and the progestogen is administered at a separate time from any one of the divided doses of estriol.

Similarly, when the estriol and the placebo are formulated separately, they can be administered essentially simultaneously, or they can be administered sequentially with respect to each other. For example, in one embodiment the subject is administered six 2 mg capsules of estriol and one placebo essentially simultaneously. In an embodiment, the subject is administered estriol in divided doses, e.g., three 2 mg capsules twice daily, and the placebo is administered essentially simultaneously with one of the divided doses of estriol. In yet another embodiment, the subject is administered estriol in divided doses, e.g., three 2 mg capsules twice daily, and the placebo is administered at a separate time from any one of the divided doses of estriol.

In certain embodiments, the estriol and the progestogen are formulated together. For oral administration, a given dose of each component, formulated together, can comprise one or more pills, tablets, capsules, or the like (i.e., unit doses). For example, a 12 mg dose of estriol and a 0.7 mg dose of norethindrone can be coformulated and administered as four capsules, each containing 3 mg estriol and 0.175 mg norethindrone, though preferably, where applicable, they are coformulated as one unit dose comprising both the estriol and the progestogen.

In certain embodiments, e.g., where a placebo is administered with the estriol on days when progestogen is not administered, the estriol and the placebo are formulated together. For oral administration, a given dose of each component, formulated together, can comprise one or more pills, tablets, capsules, or the like (i.e., unit doses). For example, a 12 mg dose of estriol and a placebo can be coformulated and administered as four capsules, each containing 3 mg estriol and a suitable amount of placebo.

When a given dose of any coformulation of estriol and progestogen (or placebo) involves administration of more than a single unit dose, e.g., four capsules, each containing 3 mg estriol and 0.175 mg norethindrone, the individual unit doses can be administered at essentially the same time, or they can be administered at different times on a given day, provided the entire daily dose is administered within a single day. For example, four capsules, each containing estriol and progestogen (or placebo) can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

VII. Clinical Evaluation of Multiple Sclerosis

Clinically, MS can be assessed and monitored using any of a number of structural (anatomical) and functional tests, including, without limitation: magnetic resonance imaging (MRI); Paced Serial Addition Test (PASAT); symbol digit modalities test (SDMT); expanded disability status score (EDSS); multiple sclerosis functional composite (MSFC); 25-foot walk test; 9-hole peg test; low contrast visual acuity; MS Quality of Life; Modified Fatigue Impact Scale; Beck Depression Inventory; 7/24 Spatial Recall Test; Benton Forms F & G; Buschke Selective Reminding Test; Verbal Paired Associates; Word List Generation. Recently, the PASAT test of cognitive function has come under criticism by some for its test-retest reliability and practice effect whereby one naturally improves over time with repeated test taking. Polman C H et al., *Neurology* 74 Suppl 3: S8-15 (2010). In some embodiments, assessment of MacDonald dissemination in space and time finds use in the present methods. For example, for dissemination in space, lesion imaging, such as, by way of illustration, Barkhof-Tintore M R imaging criteria, may be used. For instance, the following criteria can be evaluated: (1) at least one gadolinium-enhancing lesion or 9 T2 hyperintense lesions; (2) at least one infratentorial lesion; (3) at least one juxtacortical lesion; (4) at least 3 periventricular lesions; and (5) a spinal cord lesion. Such imaging criteria can optionally be used in combination with evaluation for immunoglobulin abnormalities in the cerebrospinal fluid (CSF), for example. For dissemination in time, MR imaging can also be used. For example, if an MR imaging scan of the brain performed at ≥3 months after an initial clinical event demonstrates a new gadolinium-enhancing lesion, this may indicate a new CNS inflammatory event, because the duration of gadolinium enhancement in MS is usually less than 6 weeks. If there are no gadolinium-enhancing lesions but a new T2 lesion (presuming an MR imaging at the time of the initial event), a repeat MR imaging scan after another 3 months may be needed with demonstration of a new T2 lesion or gadolinium-enhancing lesion. In various embodiments, any one or more of these structural (anatomical) and functional tests may be used in conjunction with the present invention (e.g., to assess the effectiveness of a disclosed treatment method).

Having now described the present invention in detail, the same will be more clearly understood by reference to the following examples, which are included herewith for purposes of illustration only and are not intended to limit the invention.

EXAMPLES

Example 1—Use of Glatiramer Acetate (GA) and Estriol for the Treatment of Multiple Sclerosis This example describes a randomized, double-blind, placebo-controlled human clinical trial for the treatment of multiple sclerosis using glatiramer acetate (GA) and estriol.

Enrollment Criteria

Eligible patients were females, an age of 18-50 years, a diagnosis of relapsing-remitting multiple sclerosis as defined according to the McDonald criteria (Polman C. et al., Neurology 64:987 (200)), a baseline score of 0 to 4.5 on the Expanded Disability Status Scale (EDSS, which ranges from 0 to 10, with higher scores indicating more severe disability), and disease activity as evidenced by at least two documented relapses in the previous 24 months before screening or as evidenced by at least one documented relapse within 24 months before screening with a history of at least one gadolinium-enhancing lesion on a brain or cord magnetic resonance imaging (MRI) scan performed at least 3 months before or 3 months after the clinical relapse. Key exclusion criteria were progressive forms of multiple sclerosis, other clinically significant diseases, pre-specified laboratory test abnormalities, possible malignancy on mammogram or uterine ultrasound, exposure to glatiramer acetate for longer than 2 months before randomization, relapse or steroid use within 30 days prior to randomization, use of any interferon, adrenocorticotropic hormone (ACTH), corticosteroids, intravenous immunoglobulins, or other listed MS treatments within 2 months before screening, those who were pregnant, breastfeeding, or trying to get pregnant, those not willing to discontinue other hormonal treatments, those who underwent surgical or natural menopause for longer than 1 or 3 years, respectively, with no hormone replacement therapy, and those who had ever been treated with a major immunosuppressive contraindicated treatment.

TABLE 1

Baseline Characteristics of the Intention-to-Treat Population.*

| Patient Characteristics | Estriol + GA (N = 82) | Placebo + GA (N = 76) |
|---|---|---|
| Age - yr | 37.7 ± 7.6 | 37.1 ± 7.3 |
| Race - no. (%)† | | |
| Caucasian | 65 (79.3) | 62 (81.6) |
| Black | 9 (11.0) | 7 (9.2) |
| Hispanic | 7 (8.5) | 6 (7.9) |
| Other | 1 (1.2) | 1 (1.2) |
| Time since diagnosis - yr | 3.3 ± 4.6 | 2.9 ± 4.5 |
| Number of previous relapses | | |
| Within 1 yr before screening | 1.5 ± 0.7 | 1.5 ± 0.7 |
| Within 2 yr before screening | 2.0 ± 0.7 | 2.3 ± 0.9 |
| Prior GA treatment | | |
| Never | 25 (30.5) | 27 (35.5) |
| Previously | 17 (20.7) | 6 (7.9) |
| During screening | 40 (48.8) | 43 (56.6) |
| Prior treatment with any interferon - no. (%)‡ | | |
| No | 59 (72.0) | 50 (65.8) |
| Yes | 23 (28.0) | 26 (34.2) |
| Mean score on EDSS¶ | 2.2 ± 1.2 | 2.1 ± 1.1 |
| EDSS sore at baseline - no. (%)¶ | | |
| 0 | 9 (11.0) | 6 (7.9) |
| 1.0 or 1.5 | 16 (19.5) | 21 (27.6) |
| 2.0 or 2.5 | 27 (32.9) | 24 (31.6) |
| 3.0 or 3.5 | 25 (30.5) | 22 (29.0) |
| 4.0 | 4 (4.9) | 2 (2.6) |
| 5.5 | 1 (1.2) | 1 (1.3) |
| Gadolinium-enhancing lesions number | 1.0 ± 2.3 | 0.9 ± 2.0 |
| Active lesions on brain MRI - no. (%) | | |
| No | 55 (67.9) | 53 (70.7) |
| Yes | 26 (32.1) | 22 (29.3) |
| Volume of lesions on T2 weighted Images - cm$^3$ | 6.8 ± 8.9 | 7.7 ± 11.2 |

*Plus-minus values are means +/− SD. All patients were included as the intention-to-treat population who underwent randomization, except those with no data after randomization. There were no significant differences between baseline clinical or demographic characteristics between the study groups.
†Race was self-reported.
‡Patients may have received more than one prior multiple sclerosis medication. Patients may have received other non-approved therapies for multiple sclerosis before enrollment in the study. The percentage of patients receiving medication for multiple sclerosis before study entry was balanced across treatment groups.
¶Scores on the Expanded Disability Status Scale (EDSS) ranged from 0 to 10, with higher scores indicating a greater degree of disability. The baseline EDSS score was higher than inclusion criteria of 4.5 in two patients (EDSS = 5.5), one in each study group that were 4.5 at first screening visit, but 5.5 at baseline. One patient in the Estriol + GA group did not have a confirmed relapse within 24 months prior to randomization, with enrollment based on disease activity evidenced by MRI enhancing lesions.

Study Design

Figure 1B:
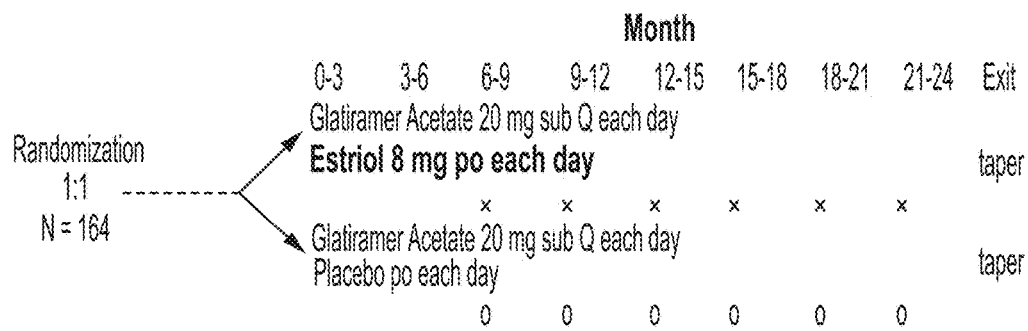

Sixteen sites randomized subjects 1:1 to oral estriol (8 mg daily) or oral placebo for 24 months (FIG. 1). A four week taper commenced at month 24 for both estriol and placebo. To avoid taking unopposed estrogens, the Estriol+GA subjects also received a progestin (0.7 mg norethindrone) daily for two weeks duration every three months starting at month 6, and Placebo+GA received a second placebo for progestin. All started GA injections (20 mg/day per day) within 2 months of randomization. Randomization had one stratification factor, GA treatment during screening. Each study site had separate examining and treating neurologists unaware of assignment. The examining neurologists performed neurologic assessments including EDSS, while treating neurologists managed patient care including treatment of relapses.

Efficacy Measures

Standardized neurologic assessments, including an EDSS assessment, were performed at months 0, 3, 6, 12, 18 and 24, and at the time of a suspected relapse (as an additional unscheduled visit). EDSS assessments were performed by physicians who were trained either by in-person training or online (www.Neurostatus.net). MRI scans were obtained at screening and at months 0, 3, 6, 12 and 24. Subjects were seen or contacted every 3 months for compliance assessments and for dispensing medications.

The primary efficacy end point was the annualized relapse rate. A relapse was defined as the appearance of new neurological symptoms or the worsening of pre-existing symptoms, lasting at least 48 hours in a subject who had been neurologically stable or improving in the previous 30 days, accompanied by an objective change in a neurological examination (i.e., a worsening of 0.5 or more points on the EDSS or a worsening by 1.0 or more points on the pyramidal, cerebellar, brainstem or visual functional system scores, not due to fatigue alone and not associated with fever or infection). The treating physician made the decision concerning whether the relapse criteria had been met, incorporating whether a change in EDSS had been documented by the examining physician. Both treating and examining physicians were unaware of study group assignments. The standard treatment for relapse was a 3-5 day course of glucocorticoids at the discretion of the treating neurologist.

Secondary efficacy end points included the proportion of subjects with a relapse over all 24 months, the proportion of subjects with positive MRI scans for gadolinium enhancing lesions, a change in PASAT cognitive testing, a sustained improvement in PASAT cognitive testing (as defined by an increase of at least 3 points sustained over at least 6 months), a change in EDSS scores from baseline, disability progression (as defined by an increase in EDSS of at least 1.0 point in subjects with a baseline score of 1.0 or higher, or by an increase of at least a 1.5 points in subjects with a baseline score of 0, each sustained for at least 6 months). Tertiary end points included gray matter atrophy on MRI, and changes in results from baseline on questionnaires including the Modified Fatigue Impact Scale, Beck Depression Inventory, and MS Quality of Life.

Safety and Adverse Events

Safety assessments, including clinical, blood laboratory safety testing and assessments of estriol levels, occurred at months 0, 3, 6, 12, 18, and 24. On study blood tests included complete blood count (CBC) with differential and platelets; chemistry panel including sodium, potassium, creatinine, BUN, glucose, total protein, albumin, bilirubin (total), alkaline phosphatase, AST (SGOT), and ALT (SGPT), and lipid profile (HDL, LDL and triglycerides, cholesterol. Gynecologic exams were done at month 0, 6, 18 and at month 24 exit, with uterine ultrasounds at months 6, 18 and at month 24 exit. Mammograms were done in screening and at month 24 exit. Adverse event analysis was based on the percentage of patients who discontinued the study and the percentage of patients who discontinued the study possibly due to adverse events.

Statistical Analysis

The sample size was determined based on the primary end point of annualized relapse rate. A total sample of 150 eligible patients would provide approximately 80% power at a two-sided significance level of 0.10 for this phase II clinical trial to detect the difference in the annualized relapse rate of 0.76 versus 1.18 for Estriol plus GA group and the Placebo plus GA group in 2 years.

Intention-to-treat analyses were carried out for all end points. For the primary endpoint, a negative binomial regression model was used to compare both 12 months and 24 months annualized relapse rates between Estriol+GA versus Placebo+GA groups adjusted for covariates. To control the overall type I error, a sequential testing procedure was applied. A hierarchical statistical approach was used whereby results in the first 12 months of treatment would be assessed, and, if and only if, significance were met, results in the entire 24 months of treatment would be assessed. The earlier timepoint was compared first since GA requires time to reach full efficacy, potentially providing a greater window to detect efficacy 12 months after initiation of GA and study drug treatment. Consistent with a phase 2 study using a clinical outcome, a p-value<0.10 was considered statistically significant.

For the time to first relapse analysis, Kaplan Meier curves and log-rank test were used to estimate and compare the relapse free probabilities of the two treatment groups. Cox proportional hazards model was used to compare the time to relapse free probabilities between two groups adjusting for covariates. The fixed effects include treatment groups (Estriol+GA vs Placebo+GA), baseline lesion number, age and baseline EDSS score. The random effect of subject is included in the model to account for within subject correlation.

Mixed effects negative binomial regression model and linear mixed effects model were used to compare enhancing lesion volume (log-transformed) between treatment groups at all follow-ups, and mixed effects logistic model was used to compare the number of subjects positive for gadolinium enhancing lesions. Linear mixed effects model was carried out to compare the percent change in whole gray matter and cortical gray matter between treatment groups. For the exploratory endpoints of EDSS, PASAT, fatigue, depression, quality of life and brain volume measures, linear mixed effects model was used to compare treatment groups at 12 and 24 months.

Mixed effects models were used to assess the association among outcomes and estriol levels at all follow-ups and using subjects in both treatment groups. Mixed effects logistic regression model was used to evaluate the association between the number of enhancing lesions and the occurrence of relapse at all follow-up intervals. Linear mixed effects model was carried out to evaluate the association between PASAT change and percent brain volume change, as well as between PASAT change and estriol levels.

Multiple imputation on the missing data was also performed according to the pattern mixture model as a sensitivity analysis. The pattern mixture model provides the analysis with the possibility of non-random dropout. The missing data were sequentially imputed by the follow up time and the imputation model assumed that the treatment effect for patients after drop out is the same as taking placebo.

Results

Patients

A total of 164 patients were randomized, of which 158 received study drug and had at least one visit thereafter (intention-to-treat population). Of the 158 patients, 82 were assigned to the Estriol+GA group and 76 to the Placebo+GA group (FIG. 1). Baseline demographics and disease characteristics were well balance across both patient groups (Table 1).

The rate of discontinuation was similar between groups (FIG. 1). A total of 60 patients (73.2%) in the Estriol plus GA group and 56 (73.7%) in the Placebo plus GA group completed the 24 month study treatment duration. Of the 158 patients, 15.8% discontinued the study during the first year (7.6% in the Estriol plus GA group and 8.2% in the Placebo plus GA group), and an additional 10.7% discontinued the study during the second year (6.3% and 4.4%, respectively). Reasons for discontinuation did not differ between groups. The most common reasons for discontinuation were lost to follow up or patient's decision based on family issues or time constraints.

Efficacy

Estriol Levels

Figure 2A:
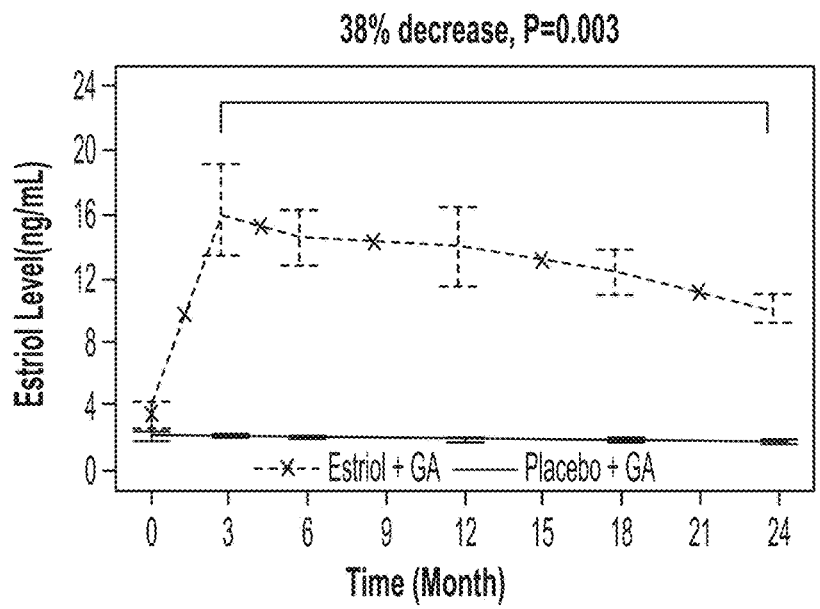
FIG. 2. Estriol levels and relapsing disease activity in Estriol+glatiramer acetate (GA) as compared to Placebo+GA treatment groups.

At month 3, serum estriol concentrations increased to a mid-pregnancy range in the Estriol plus GA treated group, while serum estriol concentrations did not exceed the estriol assay detection limit in the Placebo plus GA group (FIG. 2A; Table 2).

TABLE 2

| | Estriol Levels | | | |
|---|---|---|---|---|
| | Estriol + GA Group | | Placebo + GA Group | |
| Month | # pts | Mean ± SD, Median | # pts | Mean ± SD, Median |
| 0 | 77 | 3.5 ± 6.0, 1.8 | 68 | 2.1 ± 2.3, 1.6 |
| 3 | 77 | 16.2 ± 25.3, 11.4 | 68 | 2.1 ± 1.6, 1.8 |
| 6 | 77 | 14.6 ± 14.8, 10.6 | 67 | 1.9 ± 1.4, 1.8 |
| 12 | 67 | 13.9 ± 19.3, 10.2 | 58 | 2.0 ± 1.4, 1.8 |
| 18 | 60 | 12.4 ± 9.8, 11.7 | 51 | 1.8 ± 1.2, 1.8 |
| 24 | 58 | 10.1 ± 6.9, 9.4 | 51 | 1.8 ± 1.1, 1.6 |

Serum total estriol levels are expressed as means+/−SE in units of ng/mL. Free estriol levels were also measured and followed a similar pattern of change within individuals as total levels, with absolute free levels a fraction of the magnitude of the absolute total levels as expected.

Estriol levels remained elevated through months 3, 6 and 12 in the Estriol plus GA group. However, by month 18, there was a trend for a decrease in estriol levels (p=0.065), which reached significance by month 24, with a drop of 38% from month 3 to 24 (16.2 ng/mL at month 3, 10.1 ng/mL at month 24, p=0.003). Possible reasons for the significant drop in estriol levels at month 24 in the Estriol plus GA group included drop out of those with relatively higher estriol levels prior to month 24 or poorer compliance in those who remained in the study at month 24. To distinguish between these two possibilities, estriol levels were reexamined only in those who completed the study, and again estriol levels were again significantly decreased (p=0.0006), thereby suggesting poorer compliance at month 24 in those who remained in the study. Assessment of compliance using pill return counts showed that over 75% of those patients with a reduction in estriol levels by greater than 40% at month 24 did not have pill return counts showing compliance, while in those without such reductions in estriol levels, over 75% had pill return counts showing compliance at month 24. Compliance assessment revealed very strong correlations between and estriol levels and compliance in Estriol+GA (P=0.001), but not in Placebo+GA, with an equal rate of compliance at month 24 in Estriol+GA (0.88) and Placebo+GA (0.89).

Relapses

The primary outcome measure for efficacy was annualized relapse rate including all subjects on an intent-to-treat basis. The study was powered using alpha of 0.10 as recommended for Phase 2 trials. Since all subjects were starting GA treatment at the time of randomization to either Estriol or Placebo, and since GA treatment is known to take time to reach full potency in reducing disease activity, a hierarchical statistical approach was used whereby results in the first 12 months of treatment would be assessed, and if significance were met, results in the entire 24 months of treatment would be assessed. In the first 12 months of treatment, the relapse rate was reduced by 47% (P=0.021) in the Estriol plus GA group as compared to the Placebo plus GA group (FIG. 2B; Table 3). In the entire 24 months of treatment, the relapse rate was reduced by 32% (P=0.098) in the Estriol plus GA group as compared to the Placebo plus GA group.

Figure 2B:
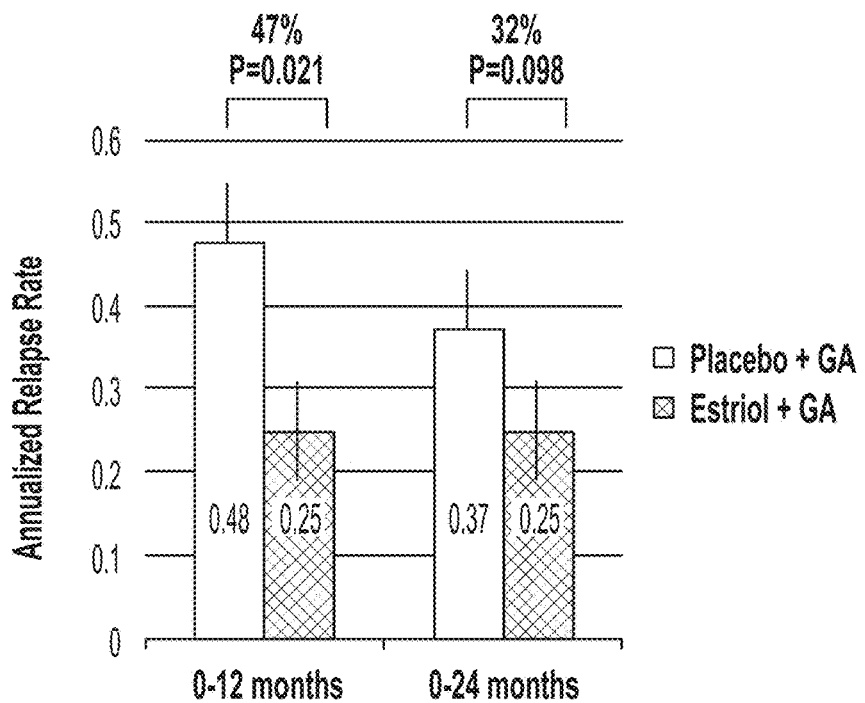
Figure 2C:
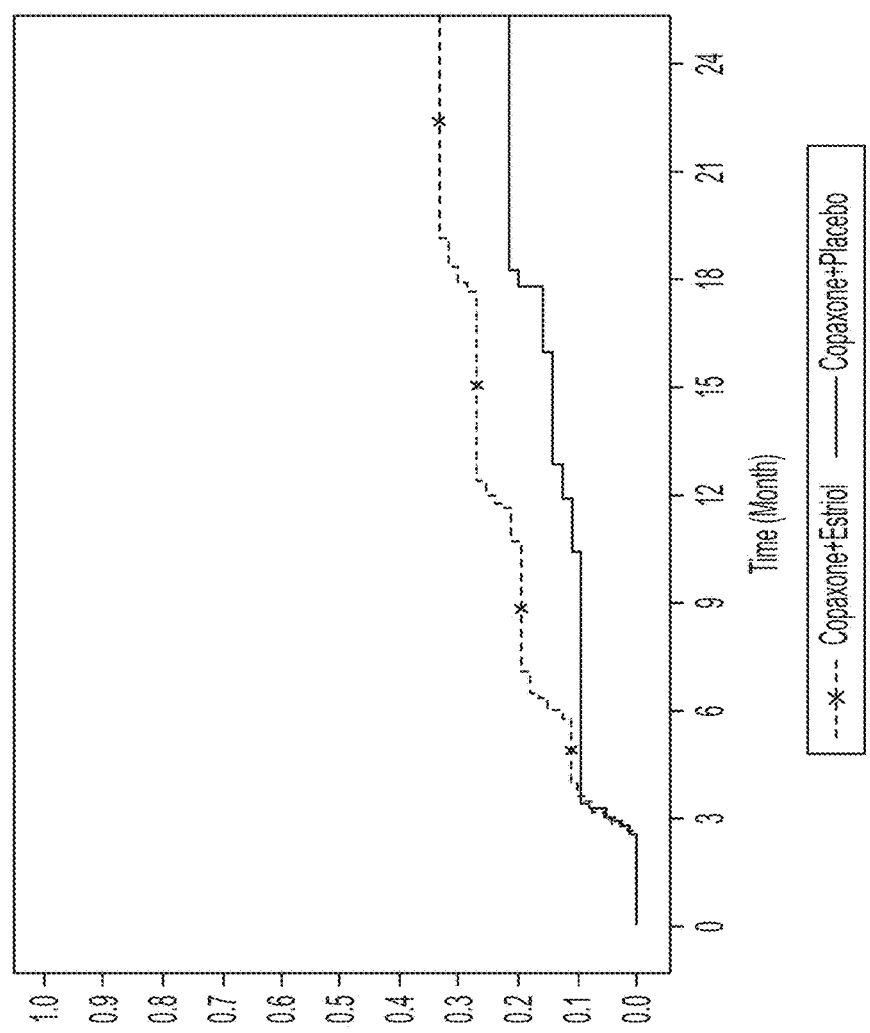

Regarding temporal patterns, relapse rates remained low and unchanged from month 12 (0.25) to month 24 (0.25) with Estriol+GA, while relapse rates decreased gradually from month 12 (0.48) to month 24 (0.37) with Placebo+GA. A more rapid onset of efficacy with Estriol+GA was also observed when examining the proportion of subjects relapse free over 24 months, with differences beginning at 6-12 months, favoring Estriol+GA, P=0.096, (FIG. 2C).

The more rapid onset of efficacy with Estriol+GA was also observed for white matter gadolinium enhancing lesions on brain MRI. In Placebo+GA, the number of subjects with enhancing lesion positive MRIs gradually decreased from baseline to month 12 to month 24, while in Estriol+GA, the number was reduced markedly by month 12, with levels remaining low and stable at month 24, Table 3. Also, enhancing lesion volumes were decreased at month 12 by 45% with Placebo+GA and by 67% with Estriol+GA. The earlier reduction in enhancing lesion activity with Estriol+GA was consistent with the earlier reduction in relapse rates with Estriol+GA, and a significant association between relapses and the presence of enhancing lesions was found (P=0.04).

TABLE 3

Clinical and MRI End Points*

| End Point | Estriol + GA (n = 82) | Placebo + GA (n = 76) |
|---|---|---|
| Annualized relapse rate in 12 months | | |
| Rate (95% CI)† | 0.25 (0.16-0.40) | 0.48 (0.33-0.69) |
| Adjusted rate ratio E + GA vs. P + GA (95% CI)§ | 0.51 (0.29-0.90)*[1] | |
| Annualized relapse rate in 24 months | | |
| Rate (95% CI)† | 0.25 (0.17-0.37) | 0.37 (0.25-0.53) |
| Adjusted rate ratio E + GA vs. P + GA (95% CI)§ | 0.65 (0.39-1.08)*[2] | |
| Time to first confirmed relapse | | |
| Proportion of pts with relapse at 12 months % (95% CI)‡ | 22.8 (15.0-33.7) | 33.1 (23.5-45.2) |
| Proportion of pts with relapse at 24 months % (95% CI)‡ | 33.3 (23.8-45.4) | 42.9 (32.1-55.5) |
| Adjusted hazard ratio E + GA vs. P + GA (95% CI)¶ | 0.63 (0.36-1.09)*[3] | |
| Time to disability progression | | |
| Proportion of pts with progression at 24 months % (95% CI)‡ | 11.4 (5.9-21.7) | 15.8 (8.8-27.6) |

TABLE 3-continued

Clinical and MRI End Points*

| End Point | Estriol + GA (n = 82) | Placebo + GA (n = 76) |
|---|---|---|
| Adjusted hazard ratio E + GA vs. P + GA (95% CI)¶ | 0.81 (0.32-2.07) | |
| EDSS score reduction from baseline to Month 24 | | |
| Mean ± SD, Median | 0.29 ± 0.98, 0.5 | 0.05 ± 1.13, 0.0 |
| Lesion activity on brain MRI Percentage patients with enhancing lesions % (95% CI) | | |
| Baseline | 32.1 (21.9-42.3) | 29.3 (19.0-39.6) |
| Month 12 | 14.5 (6.2-22.8)# | 21.0 (10.8-31.1) |
| Month 24 | 14.6 (5.2-23.9) | 14.6 (5.2-23.9) |
| Enhancing lesion volume (mean ± SD, median) | | |
| Baseline | 79.7 ± 220.0, 0 | 49.9 ± 121.2, 0 |
| Month 12 | 26.0 ± 153.5, 0 | 27.4 ± 147.2, 0 |
| Month 24 | 33.2 ± 115.9, 0 | 17.9 ± 71.1, 0 |

*Plus-minus values are means ± SD. CI denotes confidence interval, E + GA for Estriol + GA, and P + GA for Placebo + GA.
†Annualized relapse rates were calculated based on negative binomial regression.
§Relapse rate ratio was estimated using negative binomial regression with adjustment for age, baseline EDSS (<2 vs. ≥2), number of relapse 12 months prior study entry (0-1 vs. >1), MS duration (<1 vs. ≥1 year), prior GA treatment (never vs. past/current), and prior interferon treatment (yes vs. no).
‡Values were calculated using the Kaplan-Meier product-limit method. Progression defined as EDSS increase of at least 1.0 point in subjects with baseline score of 1.0 or higher or increase of at least 1.5 points with baseline score of 0, each sustained for at least 6 months.
¶Hazard ratio was estimated using Cox proportional hazard regression. For relapse, age, baseline EDSS (<2 vs. ≥2), number of relapse 12 months prior study entry (0-1 vs. >1), MS duration (<1 vs. ≥1 year), prior GA treatment (never vs. past/current), and prior interferon treatment (yes vs. no) were adjusted; for EDSS progression, age and baseline EDSS (<2 vs. ≥2) were adjusted.
*[1]P = 0.021;
*[2]P = 0.098;
*[3]P = 0.096
P = 0.14 comparing the difference between the two groups at Month 12 using mixed effect logistic model adjusted for age and baseline number of gadolinium enhancing lesions.

Disabilities

Exploratory disability outcomes revealed promising trends for improvement in the Estriol plus GA group. The Expanded Disability Status Scale (EDSS) is a standard composite disability score used extensively in MS trials. Higher scores indicate worse disability. The probability of disability worsening or EDSS progression (as defined by an increase in EDSS of 1 point for over 6 months) was 15.8% for the Placebo plus GA group, and 11.4% for the Estriol plus GA group (Table 3). EDSS scores were then assessed for possible improvement with combination treatment. While EDSS scores in the Placebo plus GA group were stable and unchanged over the entire 24 month treatment duration, the Estriol plus GA group showed a significant improvement in EDSS scores by the end of study, month 24, with a median change in EDSS of a half step (EDSS absolute median change=−0.5, p=0.03); however, group differences in EDSS improvement were not powered for significance (FIG. 3A).

Exploratory clinical outcomes showed beneficial trends in the Estriol plus GA group. The Modified Fatigue Impact Scale (MFIS) total scores revealed significant improvement by end of study month 24 in the Estriol plus GA group (p=0.01), with no change in the Placebo plus GA group (p=NS), with a significant between group difference (p=0.03) (FIG. 3B). Beck Depression Inventory (BDI) total scores and MS Quality of Life (MSQOL) scores also showed beneficial trends (FIG. 4C and Table 4).

Figure 5:
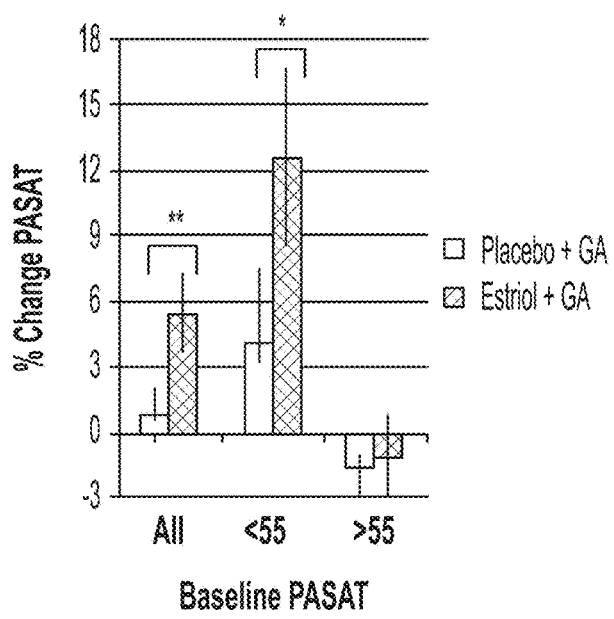
FIG. 5. Change in PASAT: Subgroups by Baseline Performance.

There were no significant differences between groups in the Multiple Sclerosis Functional Composite (MSFC), which reflects a composite of scores including the Paced Auditory Serial Addition Test (PASAT) for cognition, the 9 hole peg test and the 25 foot walk test (Table 4). However, an interesting effect of combination treatment was observed on cognitive disability. A perfect PASAT score is 60, with scores lower than 55 serving as a continuous variable for disability. By 12 months of treatment, PASAT scores improved significantly as compared with scores at baseline, among patients receiving Estriol plus GA, while no significant improvement was observed in those receiving Placebo plus GA, (p=0.04 between group difference, all adjusted for covariates of age, education and baseline scores). Subgroup analysis showed that this improvement in PASAT scores in the Estriol plus GA group at month 12 was due to improvements in those with more cognitive disability at baseline (FIG. 5). This beneficial effect on PASAT scores at 12 months in the Estriol plus GA group could not be attributed to practice effects of repeated testing since the comparison was with the Placebo plus GA group tested at identical time points.

Figures 3A, 3B, 3C:
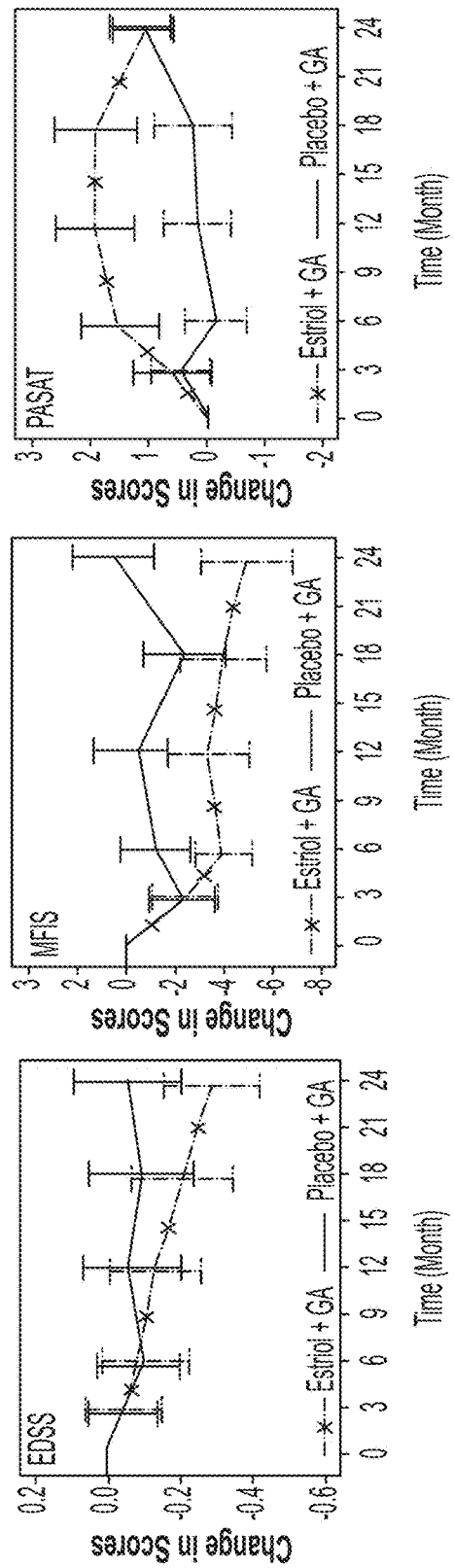
FIG. 3. Disabilities and Brain Volumes.
Figure 4A:
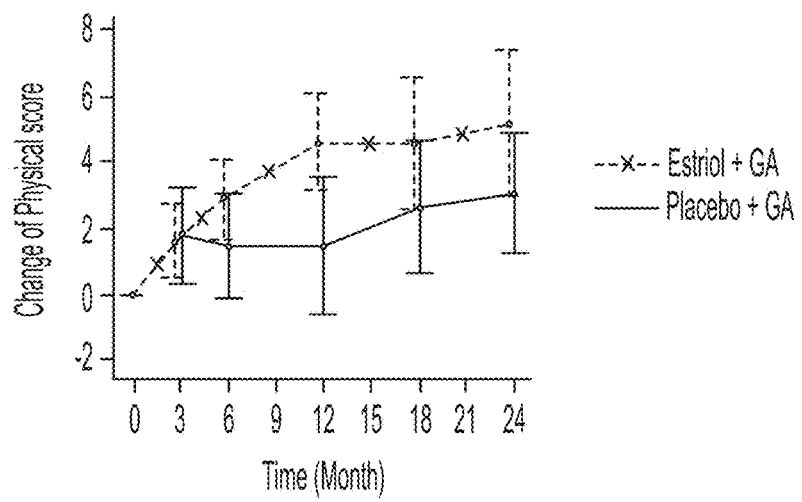
FIG. 4. Trends for MS Quality of Life and Depression.
Figure 4B:
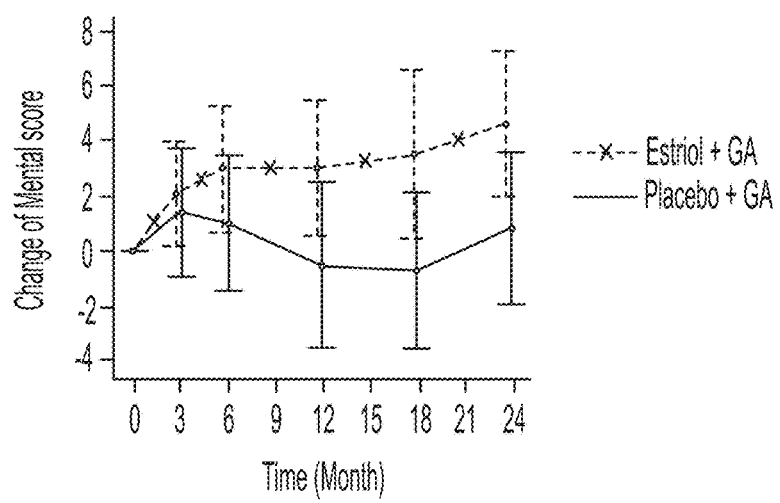
Figure 4C:
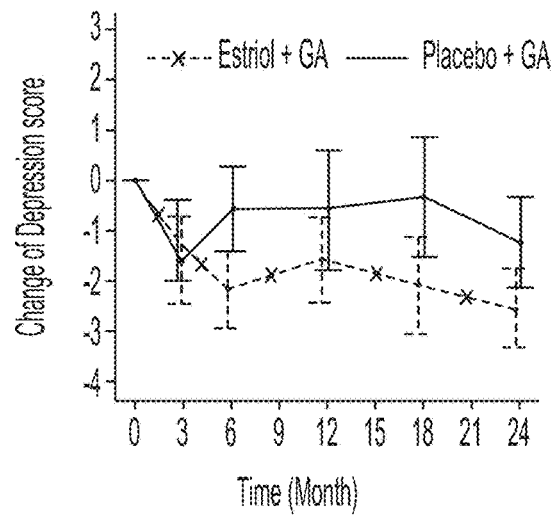

In contrast to month 12 observations, absolute PASAT scores were no different at month 24 in the Estriol plus GA group compared to the Placebo plus GA group (FIG. 3C; Table 4). This was due to both a trend for improvement in the Placebo plus GA group as well as a trend for worsening in the Estriol plus GA group. To address whether a trend for worsening in the Estriol plus GA group at month 24 might be related to the decrease in estriol levels at month 24 (FIG. 2A), correlations between estriol levels and improvement in PASAT scores were assessed. Indeed, higher estriol levels correlated with greater improvement in PASAT scores (p=0.03 for all patients; p=0.07 for Estriol+GA patients only). Further, when serum estriol levels were dichotomized to greater than or less than 6 ng/mL, estriol levels greater than or equal to 6 ng/mL correlated strongly with improvement in PASAT scores (All patients, p=0.009; Estriol plus GA group, p=0.006).

Gray matter volumes, specifically cortical gray matter volumes, have previously been associated with cognitive

TABLE 4

| End Point | Multiple Sclerosis Functional Composite (MSFC) | |
|---|---|---|
| | Estriol + GA (N = 82) | Placebo + GA (N = 76) |
| MSFC Score[a] | | |
| Baseline score (Mean ± SD, Median) | −0.04 ± 0.69, 0.05 | 0.06 ± 0.79, 0.24 |
| Change from baseline at Month 12 | N = 70 | N = 58 |
| Mean ± SD, Median | 0.13 ± 0.37 | 0.06 ± 0.38 |
| Change from baseline at Month 24 | N = 60 | N = 54 |
| Mean ± SD, Median | 0.10 ± 0.35 | 0.09 ± 0.43 |
| PASAT3 score - All Patients[a] | | |
| Baseline score (Mean ± SD, Median) | 51.0 ± 8.9, 55 | 52.3 ± 9.1, 56 |
| change from baseline at Month 12 | N = 70 | N = 61 |
| Mean ± SD, Median | 1.9 ± 5.6, 1.0** | 0.1 ± 4.5, 0 |
| change from baseline at Month 24 | N = 60 | N = 55 |
| Mean ± SD, Median | 1.1 ± 4.0, 1.0 | 1.1 ± 4.3, 0 |
| % change from baseline at Month 12 | N = 70 | N = 61 |
| Mean ± SD, Median (%) | 5.5 ± 15.6, 1.8** | 0.8 ± 9.9, 0 |
| % change from baseline at Month 24 | N = 60 | N = 55 |
| Mean ± SD, Median (%) | 2.9 ± 10.6, 1.7 | 2.7 ± 10.3, 0 |
| PASAT3 score - Patients with baseline score <55[a] | N = 39 | N = 33 |
| Baseline score (Mean ± SD, Median) | 43.7 ± 7.6, 45 | 44.7 ± 9.1, 49 |
| change from baseline at Month 12 | N = 33 | N = 25 |
| Mean ± SD, Median | 4.7 ± 6.6, 4.0* | 1.6 ± 6.0, 1.0 |
| change from baseline at Month 24 | N = 26 | N = 23 |
| Mean ± SD, Median | 2.3 ± 5.2, 3.5 | 3.0 ± 5.9, 4.0 |
| % change from baseline at Month 12 | N = 33 | N = 25 |
| Mean ± SD, Median (%) | 12.6 ± 19.9, 7.6* | 4.0 ± 14.0, 3.8 |
| % change from baseline at Month 24 | N = 26 | N = 23 |
| Mean ± SD, Median (%) | 6.4 ± 14.8, 6.8 | 6.9 ± 14.7, 9.1 |
| 9-Hole Peg Test[b] | | |
| Baseline value (Mean ± SD, Median) | 19.7 ± 3.8, 19.0 | 19.1 ± 2.7, 18.8 |
| Change from baseline at Month 12 | N = 70 | N = 63 |
| Mean ± SD, Median | −0.6 ± 1.5, −0.6 | −0.1 ± 1.8, −0.4 |
| Change from baseline at Month 24 | N = 60 | N = 56 |
| Mean ± SD, Median | −0.1 ± 3.5, −0.6 | −0.4 ± 1.5, −0.5 |
| 25-foot Walk Time[b] | | |
| Baseline value (Mean ± SD, Median) | 4.9 ± 1.0, 4.7 | 4.9 ± 1.5, 4.5 |
| Change from baseline at Month 24 | N = 70 | N = 60 |
| Mean ± SD, Median | 0.1 ± 0.8, 0.1 | 0.0 ± 0.9, 0.0 |
| Change from baseline at Month 24 | N = 60 | N = 55 |
| Mean ± SD, Median | −0.1 ± 0.6, −0.0 | 0.1 ± 1.1, 0.1 |

Figures 3H, 3I:
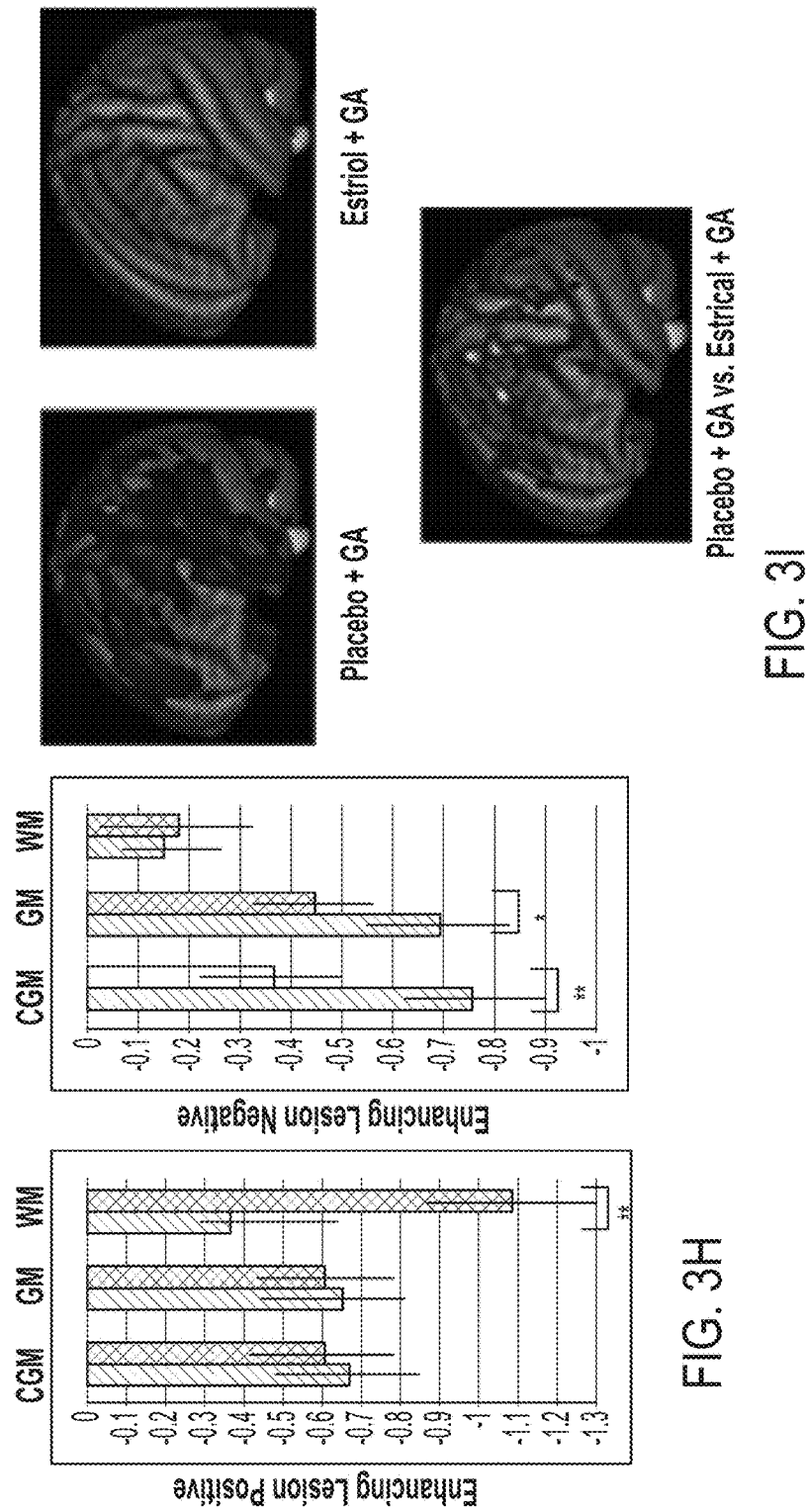
Figure 6:
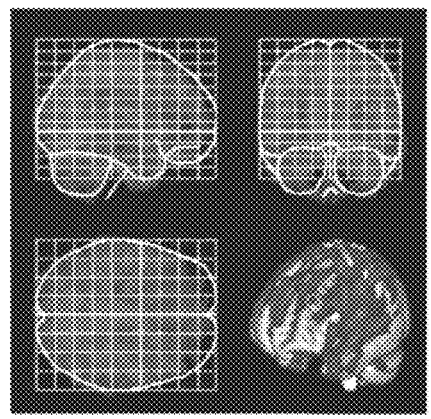
FIG. 6. Voxel-wise Gray Matter Atrophy.
Figure 6:
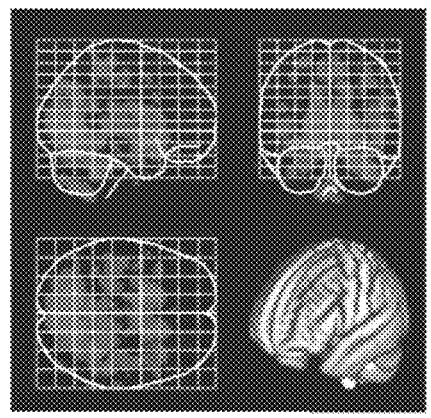
Figure 6:
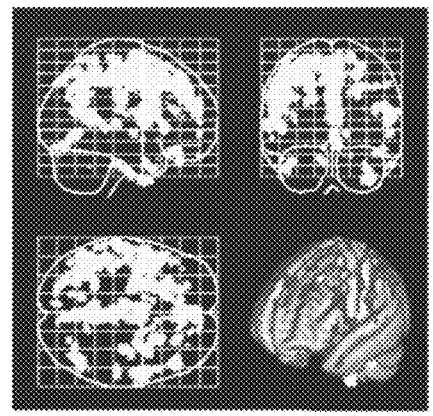

[a]Change from baseline positive value indicate improvement for MSFC and PASAT3
[b]Change from baseline positive value indicate worsening for 9-Hole Peg test and 25-Foot Walk Time.
**P < 0.05, student t-test comparing the means of the two study groups
*P < 0.10, student t-test comparing the means of the two study groups
§Values were calculated using the Kaplan-Meier product-limit method.

test scores. There was less cortical gray matter atrophy (45%) and whole gray matter atrophy (30%) at month 12 in the Estriol plus GA group compared to the Placebo plus GA group (cortical gray matter: Estriol+GA=−0.41, Placebo+GA=−0.74, p=0.079; whole gray matter: Estriol+GA=−0.47, Placebo+GA=−0.68, p=0.139) (FIGS. 3D & 3E). This gray matter sparing was independently confirmed using voxel-based morphometry (VBM), the latter revealing which gray matter regions were preserved with Estriol+GA compared to Placebo+GA (FIGS. 3 and 6). Subgroup analysis showed that this gray matter sparing was present in the group of patients that were enhancing lesion negative (cortical gray matter 52%: Estriol+GA=−0.36, Placebo+GA=−0.76, p=0.048; whole gray matter 39%: Estriol+GA=−0.44, Placebo+GA=−0.70, p=0.097), while absent in the group that was enhancing lesion positive. Similar to effects on PASAT scores, beneficial effects on gray matter sparing in the Estriol+GA group were no longer present at month 24, the time when estriol levels had decreased. Indeed, correlations between PASAT improvement and gray matter sparing were found (cortical gray matter, p=0.0327; whole gray matter, p=0.0359), which was present in the Estriol+GA group (cortical gray matter, p=0.0159; whole gray matter, p=0.0093) and absent in the control Placebo+GA group. In contrast, the Estriol+GA group compared to the Placebo+GA group had more white matter atrophy, but this occurred only in patients who were enhancing lesion positive, with no differences in those who were enhancing lesion negative. Greater white matter atrophy occurring only in the enhancing lesion positive patients with Estriol+GA treatment was consistent with pseudoatrophy due to anti-inflammatory effects of Estriol+GA in white matter, which in turn was consistent with both the greater reduction in MRI enhancing lesions in white matter and greater reductions in clinical relapse rates in the Estriol+GA group (FIGS. 2B & 2C).

TABLE 5

MRI Volumes

| End point§ | Estriol + GA (N = 82) | Placebo + GA (N = 76) |
|---|---|---|
| Baseline Volume (cc)§§ | | |
| Whole brain | 1604 ± 62 | 1602 ± 51 |
| Whole gray matter | 954 ± 51 | 926 ± 52 |
| Cortical gray matter | 754 ± 46 | 761 ± 42 |
| White matter | 650 ± 35 | 640 ± 32 |
| % change - Baseline to 12 months All patients | | |
| Whole brain | −0.48 ± 0.69, −0.45 | −0.49 ± 0.63, −0.43 |
| Whole gray matter | −0.47 ± 0.82, −0.49 | −0.68 ± 0.71, −0.66 |
| Cortical gray matter | −0.41 ± 0.94, −0.49* | −0.74 ± 0.81, −0.69 |
| White matter | −0.50 ± 1.06, −0.11 | −0.21 ± 0.82, −0.15 |
| Patients without enhancing lesions at baseline | | |
| Whole gray matter | −0.44 ± 0.76, −0.45* | −0.70 ± 0.74, −0.66 |
| Cortical gray matter | −0.36 ± 0.89, −0.42** | −0.76 ± 0.85, −0.73 |
| White matter | −0.18 ± 0.94, 0.07 | −0.15 ± 0.71, −0.15 |
| Patients with enhancing lesions at baseline | | |
| Whole gray matter | −0.61 ± 0.84, −0.54 | −0.65 ± 0.64, −0.64 |
| Cortical gray matter | −0.60 ± 0.92, −0.57 | −0.67 ± 0.72, −0.69 |
| White matter | −1.08 ± 1.03, −0.92** | −0.36 ± 1.06, −0.14 |
| % change - Baseline to 24 months All patients | | |
| Whole brain | −0.87 ± 0.82, −0.99 | −0.77 ± 0.72, −0.88 |
| Whole gray matter | −0.95 ± 0.75, −0.93 | −0.95 ± 0.75, −0.93 |
| Cortical gray matter | −0.94 ± 0.87, −0.96 | −1.05 ± 0.86, −0.94 |
| White matter | −0.75 ± 1.28, −0.64 | −0.52 ± 1.12, −0.54 |
| Patients without enhancing lesions at baseline | | |
| Whole gray matter | −0.92 ± 0.80, −0.89 | −0.98 ± 0.77, −0.92 |
| Cortical gray matter | −0.93 ± 0.89, −0.97 | −1.12 ± 0.88, −0.94 |
| White matter | −0.38 ± 1.21, −0.35 | −0.46 ± 1.17, −0.48 |
| Patients with enhancing lesions at baseline | | |
| Whole gray matter | −0.99 ± 0.68, −0.98 | −0.82 ± 0.70, −0.92 |
| Cortical gray matter | −0.95 ± 0.85, −0.93 | −0.82 ± 0.80, −0.93 |
| White matter | −1.32 ± 1.31, −1.20** | −0.62 ± 0.97, −0.84 |

§Data presented as Mean ± SE, median; negative values indicate volume loss.
§§No significant difference between the two study groups for baseline volumes. Wilcoxon rank sum test.
**P < 0.05, linear mixed effects model for the difference of the two groups means, adjusted for baseline volume and enhancing lesions present or absent.
*P < 0.10, linear mixed effects model for the difference of the two groups means, adjusted for baseline volume and enhancing lesions present or absent.

Safety

Estriol plus GA was found to be safe and well tolerated with regard to adverse events including gynecological outcomes (Table 6). Regarding adverse events, irregular menses occurred more with Estriol+GA (P<0.001), while vaginal infections occurred more with Placebo+GA (P<0.05), with no increase in discontinuations due to either.

TABLE 6

Adverse Events and Serious Adverse Events

| Adverse Events† | Estriol + GA (N = 82) | Placebo + GA (N = 76) |
| --- | --- | --- |
| Any adverse event - no. of events, [no of pts, % of pts] | 480 [76, 93%] | 392 [67, 87%] |
| Most frequent events - no. of events [no of pts, % of pts] | | |
| Copaxone injection area abnormalities | 51 [26, 32%]* | 30 [14, 18%] |
| Upper respiratory infection | 33 [22, 27%] | 38 [26, 34%] |
| Irregular menses/spotting | 26 [19, 23%]*** | 4 [3, 4%] |
| Urinary tract infection | 23 [15, 18%] | 16 [10, 13%] |
| Fatigue | 15 [13, 16%] | 10 [8, 10%] |
| Depression/anxiety | 14 [12, 15%] | 10 [9, 12%] |
| Menstrual flow amount increased | 12 [11, 13%] | 8 [6, 8%] |
| Headache | 11 [9, 11%] | 12 [11, 14%] |
| Nausea/vomiting | 9 [7, 9%] | 5 [5, 6%] |
| Sinusitis | 6 [6, 7%] | 14 [10, 13%]* |
| Arm/leg numbness, tingling | 7 [6, 7%] | 10 [7, 9%] |
| Gastroenteritis | 7 [5, 6%] | 4 [3, 4%] |
| Dizziness | 5 [4, 5%] | 10 [7, 9%] |
| Vision problem (blurry, double) | 6 [4, 5%] | 7 [7, 9%] |
| Back pain | 5 [4, 5%] | 5 [5, 6%] |
| Menstrual cramp | 4 [4, 5%] | 5 [4, 5%] |
| Insomnia | 4 [4, 5%] | 4 [4, 5%] |
| Heart palpitation | 2 [2, 2%] | 4 [4, 5%] |
| Shingles | 2 [2, 2%] | 4 [4, 5%] |
| Vaginal infection | 1 [1, 1%] | 9 [8, 10%]** |
| Adverse events leading to discontinuation - no. (%) | 5 (6%) | 5 (6%) |
| Severe adverse events‡ | 9 [8, 10%] | 12 [10, 13%] |
| MS relapse | 2 [2, 2%]¶ | 6 [5, 6%]¶ |
| Pregnancy termination | 2 [2, 2%] | 0 |
| UTI | 1 [1, 1%] | 1 [1, 1%] |
| Migraine headache related eye pain | 1 [1, 1%] | 0 |
| Heart failure | 1 [1, 1%] | 0 |
| Pace maker implantation | 1 [1, 1%] | 0 |
| Pyelonephritis | 1 [1, 1%] | 0 |
| Systolic heart failure | 1 [1, 1%] | 0 |
| Accidently took other's drug | 0 | 1 [1, 1%] |
| Acute appendicitis | 0 | 1 [1, 1%] |
| B-cell lymphoma§ | 0 | 1 [1, 1%] |
| Car accident related body numbness | 0 | 1 [1, 1%] |
| Right knee replacement | 0 | 1 [1, 1%] |
| Other safety events monitored Uterus | | |
| Endometrial thickness >8 mm (ultrasound) - no. (%) | 24 (29) | 27 (36) |
| Endometrial biopsies performed§§ - no. (%) | 9 (11) | 6 (8) |

TABLE 6-continued

Adverse Events and Serious Adverse Events

| Adverse Events† | Estriol + GA (N = 82) | Placebo + GA (N = 76) |
|---|---|---|
| Fibroids (ultrasound) - no. (%) | 8 (10) | 8 (11) |
| Abnormal proliferation on biopsy - no. (%) | 0 | 0 |
| Breast | | |
| Fibrocystic disease on clinical exam | 5 (6) | 4 (5) |
| Mammogram with malignancy | 0 | 0 |

†All patients who took at least one dose of study drug were included. However, among the 6 patients who dropped shortly after baseline visit, five did not have safety evaluation data and were excluded from the safety analysis. The listed events reported by % were rounded up to nearest integer. The events are listed by decreasing incidence in the Estriol + GA group, within each category.
*AE significantly higher in one treatment group compared to the other;
***indicating $P < 0.001$,
**indicating $P < 0.05$, and
*indicating $P < 0.10$.
‡SAE patients were all hospitalized, but none had severe or immediately life-threatening condition.
§This patient, in the placebo group, discontinued the study at the time of B-cell lymphoma diagnosis when was on study for 12 months and died 17 months later.
¶In Estriol + GA group, both patients discontinued the study: one before and one after Month 12. In Placebo + GA group, 3 patients discontinued the study: 1 before and 2 after Month 12.
§§Four patients had multiple uterine endometrial biopsies: two patients had two biopsies each in the Estriol + GA group and two patients had three biopsies each in the Placebo + GA group. No abnormal proliferation was found.
Note:
No laboratory abnormalities occurred significantly more frequently in either treatment group.

Sensitivity Analysis

Original analyses included all subjects on an intention-to-treat basis. 73.6% of the subjects completed the entire 24 month treatment duration, with a total of 22 drop outs in the GA plus Estriol group and 20 drop outs in the GA plus Placebo group (FIG. 1; Table 7). This dropout rate was expected considering the unique nature of this study whereby the study only provided estriol and placebo treatments, while patients provided their own injectable GA treatment. The reason for drop out did not differ between treatment groups (FIG. 1). Sensitivity analyses for both the primary endpoint of relapse rate, as well as for other exploratory outcomes of brain volume loss and PASAT scores, each confirmed the robustness of the original analyses.

TABLE 7

Drop Outs
Subjects who completed month 24 (M 24) versus subjects who dropped after month 12 (M 12)

| Study status | Estriol + GA | Placebo + GA | Total |
|---|---|---|---|
| Completion | 60 | 56 | 116 |
| Dropped before M 12* | 12 | 13 | 25 |
| Dropped after M 12** | 10 | 7 | 17 |
| Total | 82 | 76 | 158 |

*Among the 25 subjects, 8 had M 3 visit and 17 (8 in Estriol group and 9 in placebo group) had M 6 visit.
**Among the 17 subjects, 5 (4 in Estriol group and 1 in placebo group) had M 18 visit.

Between month 12 and 24, there were 10 drop outs in the Estriol plus GA group (10/70=14.2%) and 7 drop outs in the Placebo plus GA group (7/56=12.5%). Adverse events did not differ by group when split into those before or after 12 months (Table 8). Regarding the primary outcome measure of relapse rate at end of study (month 24), the primary endpoint of a reduction in relapse rate by one third in the Estriol plus GA group as compared to the Placebo plus GA group was reached. The observation that relapse rates were reduced more dramatically, by nearly half, at the earlier time point of month 12 could have been due in part to drop outs between month 12 and 24. Thus, the effect of drop outs on the primary outcome measure of relapse rates was formally analyzed by imputing missing data due to dropout based on the pattern mixture model. This analysis sought to address the possibility of missing data not being random. Similar results were obtained in analyses with and without imputation, supporting the robustness of the results for the primary endpoint (Table 9).

TABLE 8

Adverse events split by drop out before or after 12 months

| | Estriol + GA | | Placebo + GA | |
|---|---|---|---|---|
| Body system | Completed (N = 60) | Discontinued (N = 22) | Completed (N = 56) | Discontinued (N = 20) |
| Breast | 11 [10] | | 5 [5] | |
| Cancer | | | | 1 [1] |
| Cardiovascular | 7 [5] | 2 [2] | 8 [8] | |
| GA related? | 53 [20] | 18 [8] | 22 [11] | 10 [4] |
| Endocrinology | 1 [1] | | | |
| Extremity | 41 [24] | 13 [8] | 43 [21] | 4 [2] |
| General | 50 [28] | 11 [6] | 48 [26] | 9 [6] |
| GI | 25 [14] | 6 [5] | 19 [15] | 3 [3] |
| GU | 21 [14] | 3 [2] | 17 [10] | 3 [3] |
| GYN | 16 [15] | 4 [2] | 18 [15] | 3 [3] |
| Head/Neck | 33 [20] | 5 [3] | 42 [26] | 9 [4] |
| Lymph | | | 1 [1] | 1 [1] |
| Menses | 36 [26] | 8 [5] | 14 [10] | 3 [2] |
| Mental | 17 [14] | 6 [5] | 14 [10] | 5 [5] |
| MRI related | | | 3 [2] | |
| Skeleton | 3 [3] | 1 [1] | 2 [1] | |
| Neurology | 17 [12] | 2 [2] | 13 [9] | 1 [1] |
| Respiratory | 42 [25] | 5 [4] | 47 [26] | 7 [3] |
| Skin | 19 [15] | 4 [4] | 15 [10] | 2 [2] |
| Total | 392 [58] | 88 [18] | 331 [53] | 61 [13] |

Data was presented as: Number of events [# of patients]

Sensitivity Analysis Relapse Rate

For the primary endpoint, the main analysis seeks to compare the relapse event rate between treatment groups based on the negative binomial regression. As a sensitivity analysis, recurrent events analysis was performed based on Andersen Gill model to compare the relapse hazard rate between treatment groups. Both analyses showed similar results, and significant and meaningful reduction in relapse rates was found in the Estriol plus GA group as compared to the Placebo plus GA group.

imputation model assumed that the treatment effect for patients after dropout is the same as taking placebo (Ratitch, B. & M. O'Kelly, Proc. Pharm. Industry SAS User Group, Nashville (2011)). The analyses results were compared for relapse rate with assumptions of ignorable and non-ignorable missing data. The results are similar with and without

TABLE 9

Sensitivity analysis for the primary end point - Annualized Relapse Rate

| Analysis | Method* | Missing Data Imputed | Results 0-12 Months | 0-24 Months |
|---|---|---|---|---|
| Original analysis | Negative binomial regression model | No | Relapse rate ratio 0.51 95% CI: 0.29-0.90 P = 0.021 | Relapse rate ratio: 0.65 95% CI: 0.39-1.08 P = 0.098 |
| Sensitivity analysis | Negative binomial regression model | Yes, multiple imputation based on the pattern mixture model. | Relapse rate ratio 0.56 95% CI: 0.31-1.03 P = 0.063 | Relapse rate ratio: 0.63 95% CI: 0.37-1.08 P = 0.096 |
| Sensitivity analysis | Andersen Gill model; relapse was treated as recurrent event. | No | Hazard ratio 0.49 95% CI: 0.28-0.87 P = 0.015 | Hazard ratio: 0.63 95% CI: 0.38-1.03 P = 0.067 |

*Age, baseline EDSS, number of relapse 12 months prior study entry, MS duration, prior GA treatment and prior interferon treatment were included in the model as covariates.

Missing Data Due to Dropouts

The missing data due to study dropouts complicate the statistical analysis because certain assumptions must be made about the missingness mechanism and unobserved values to deal with incomplete observations. For the primary analysis of longitudinal endpoints were based on the assumption that missing data are ignorable, which means that missingness is independent of the unobserved outcomes after accounting for the appropriate observed data in the model. Similarly, for the time to event endpoints, the Kaplan-Meier curves and proportional hazard model were based on the assumption that dropout time is non-informative and independent of the event time.

imputation, and significant and meaningful reduction in relapse rates was observed in the Estriol plus GA group as compared to the Placebo plus GA group.

Similar imputation analyses were carried out for the endpoints of brain volume change in gray matter, in cortical gray matter, and PASAT3 to evaluate the possible impact of study dropout. Table 10 compares analyses of brain volume change for gray matter and cortical gray matter. Longitudinal analyses results for PASAT3 with and without imputation were also done. The imputation analysis showed no significant improvement in the Placebo plus GA group at both 12 and 24 months.

TABLE 10

Missing data analysis for some secondary end points - Comparing the difference of means between the two study groups at Months 12 and 24

| End Point | Month | Original Data (Ignorable missing data) Estimate difference (95% CI) | Multiple imputation Data (Non-ignorable missing data) Estimate difference (95% CI) |
|---|---|---|---|
| Whole gray matter volume | 12 | 0.19 (−0.06, 0.45), P = 0.14 | 0.19 (−0.06, 0.45), P = 0.14 |
| (% change from baseline)§ | 24 | 0.10 (−0.17, 0.37), P = 0.48 | 0.13 (−0.13, 0.40), P = 0.32 |
| Cortical gray matter volume | 12 | 0.26 (−0.03, 0.55), P = 0.08 | 0.26 (−0.03, 0.55), P = 0.08 |
| (% change from baseline)§ | 24 | 0.21 (−0.10, 0.51), P = 0.19 | 0.23 (−0.07, 0.54), P = 0.13 |
| PASAT3 score | 12 | 1.5 (−0.1, 4.3), P = 0.06 | 1.6 (0.0, 3.2), P = 0.05 |
| (Change from baseline)¶ | 24 | −0.3 (−1.9, 1.4), P = 0.74 | 0.3 (−1.5, 2.0), P = 0.77 |

§Values were calculated based on linear mixed effect model adjusted for baseline volume and enhancing lesions (present vs. absent).
¶Values were calculated based on linear mixed effect model adjusted for baseline PASAT3 score.

Longitudinal Endpoints

Sensitivity analyses regarding missing data were performed to demonstrate the robustness of study conclusion. For this, multiple imputation analysis were performed on the missing data according to the pattern mixture model as a sensitivity analysis to address the possibility of data being non-ignorable or missing not at random (MNAR) (Little, R. & L. Yau, Biometrics 52:1324 (1996)). The missing data were sequentially imputed by the follow up time, and the MRI Methodologies:

MRI scans were performed at 0, 3, 6, 12 and 24 months using a standardized protocol implemented at each site that consisted of the following: T1-weighted 3D volume, pre and post contrast: TR2200, TE3.4, TI 900, 176 slices, 1 mm$^3$. Dual-echo fast spin echo: TR10000, TE12/95, 50 slices, 1×1×3 mm. Fluid attenuated inversion recovery (FLAIR): TR10380, TE88, TI88, TI2500, 50 slices, 1×1×3 mm. Minor changes were allowed to accommodate different platforms and field strengths at each site. MRI data in Dicom format were fully anonymized prior to transfer and then uploaded to the central MRI reading center database. Prior to study onset, each site provided a dummy scan utilizing the standardized sequences for review by the central MRI reading center to verify scan quality and fidelity. Quality control was maintained at each site using standard procedures for clinical scanners (daily phantoms, stability testing). Quarterly phantoms were collected from 12 of the 15 sites, most using the standard American College of Radiology (ACR) phatom. One site upgraded from a Siemens 1.5T to a 3.0T in November 2013, resulting in the acquisition of one month 24 scan on the new scanner. One site upgraded from a Phillips Achieva 3.0T to a Pillips Intera 3.0T after the first subject completed month 24. All subsequent studies were performed on the Intera.

Scans underwent a standard review locally by a radiologist blind to study details to assess for any new or unusual findings as a safety measure. Incoming imaging data was reviewed for completeness and fidelity to study pulse sequences by the imaging core investigators. Local radiologists and imaging core investigators were all blind to randomization assignment. All MRI investigators remained blinded to treatment assignment until the end of the study.

Analysis of gadolinium enhancing lesions and T2 lesions were performed as described by Sicotte et al. (Ann. Neurology 52:421 (2002)). Briefly, MRI data was coded by study site and randomization number. The number and volume of enhancing lesions were quantified on the post contrast T1 weighted scans by an experienced investigator who was blind to treatment group using a semi-automated threshold-based algorithm. To assess T2 lesions, all FLAIR images were RF corrected, then intensity normalized and registered into a common space defined by the baseline scan for each individual. All subsequent scans were registered to the baseline exam for spatial normalization using a rigid body model. T2 lesion areas were determined using a semi-automated intensity based segmentation procedure by a trained, experienced researcher verified by a single investigator (NLS).

MRI brain, whole gray matter, whole white matter and cortical gray matter volumes were determined using a pair-wise Jacobian integration (PJI) method. Pre-processing for structural T1-weighted images included 1) N3 non-uniformity correction, 2) histogram-based intensity normalization, 3) linear standard space registration using ICBM 2009c nonlinear symmetric template, 4) patch-based brain extraction, and 5) lesion-inpainting. Inputs to PJI were a pair of baseline and follow-up pre-processed structural T1-weighed images. The PJI consisted of 1) linear skull-constrained symmetric registration, 2) halfway transformation and resampling, 3) nonlinear symmetric registration using ANTS, and 4) voxelwise Jacobian determinant calculation on the warp field. Whole gray matter and whole white matter tissue masks were generated by SPM8 Segment function. Additional nonlocal means denoising was applied. For whole brain tissue masks, the whole gray matter and whole white matter masks were combined. For cortical gray matter mask, a standard cortical mask was nonlinearly transformed and merged with gray matter mask. The standard template was the ICBM (ICBM 2009c nonlinear symmetric version), and the nonlinear registration was performed by ANTS. Finally, the Jacobian determinants were averaged within the masks for percent volume change in cortical gray matter, whole gray matter, whole white matter, and whole brain.

Voxel-based morphometry (VBM) analyses were performed as described by Kurth et al. (Neuroimage Clin. 4:454 (2014)). All subjects included in the VBM cohort were required to have at least reached month 12 of the study, and all images had to pass quality control before and after image preprocessing to be included in the VBM cohort. Using this criteria, the VBM cohort consisted of 111 subjects (62 in the estriol+GA, and 49 in the placebo+GA group) from 13 sites for month 12 analyses, and 86 of these subjects (45 in the estriol+GA, and 41 in the placebo+GA group) for 24 month analyses.

Brain images were preprocessed utilizing SPM8 and the VBM8 toolbox. White matter lesions were in-painted to minimize their impact based on manual delineations that were used for the analysis of new T2 lesions. For this purpose, these manually delineated lesion masks were coregistered to the T1-weighted images, corrected if necessary, and used for lesion in-painting as described by Chard et al. (J. Magn. Reson. Imaging 34:223 (2010)). The lesion in-painted images were subsequently realigned for each subject using halfway-registrations and corrected for bias-field inhomogeneities. The realigned, bias corrected images were then tissue-classified into gray matter, white matter, and cerebrospinal fluid and registered to MNI space through linear and non-linearly transformations (see http://dbm.neuro.uni-jena.de/vbm8/VBM8-Manual.pdf). More specifically, the tissue classification was based on maximum a posteriori segmentations, accounted for partial volume effects, and was refined by applying a spatially adaptive non-local means denoising filter as well as a hidden Markov random field model. These methods made the tissue-classification independent of tissue probability maps and thus additionally minimized the influence of misclassifications, lesions, and altered geometry. Using DARTEL, the gray matter segments were then spatially normalized to the DARTEL Template supplied with the VBM8 Toolbox (see http://dbm.neuro.uni-jena.de/vbm), resulting in a voxel-wise comparability between subjects and time-points. Finally, the gray matter segments were smoothed with a Gaussian kernel (8 mm full width at half maximum). These smoothed gray matter segments constituted the input for the statistical analysis. For visualization, a mean template was created from the normalized brain images of all subjects, allowing the results from the statistical analysis to be related to the underlying mean anatomy of the subject sample. VBM Statistical Analyses.

For the statistical analysis, a general linear model was applied that used the smoothed gray matter segments as the dependent and group x time as the independent variable. Subject and scan site were added as variables of no interest, thus effectively controlling for inter-individual differences (e.g. individual anatomy, age, disease duration, etc.) as well as the potentially confounding impact of different scanners. Non-sphericity was modeled and accounted for as described previously and implemented in SPM8. Applying this model, the interaction between group and time was calculated using T-tests to investigate group differences in local gray matter changes between month 0 and month 12 (month 0 and month 24, respectively). In addition, the gray matter loss within each group was investigated by calculating T-tests for month 0>month 12 (month 0>month 24, respectively) for each group separately. All results were corrected for multiple comparisons by controlling the false discovery rate (FDR) using a threshold of $P \leq 0.05$. Corrected results were rendered on the mean template of all subjects in FIG. 3. In addition, significant findings were visualized using maximum intensity projections as shown in FIG. 6.

INCORPORATION BY REFERENCE

All patents, published patent applications, and other publications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

What is claimed is:

1. A method for reducing cortical gray matter atrophy in a human subject suffering from multiple sclerosis receiving a first estriol treatment regimen, comprising:
   obtaining a measurement of the serum estriol concentration in the subject; and
   administering a second estriol treatment regimen to the subject if the serum estriol concentration is less than 6 ng/mL;
   wherein the daily amount of estriol administered during the second estriol treatment regimen is greater than the daily amount of estriol administered during the first estriol treatment regimen.

2. The method of claim 1, wherein the first treatment regimen comprises administering to the subject, on a continuous basis throughout one or more consecutive treatment periods, about 200 µg to about 20 mg of estriol daily.

3. The method of claim 2, wherein the first treatment regimen comprises administering to the subject, on a continuous basis throughout one or more consecutive treatment periods, about 1 mg to about 10 mg of estriol daily.

4. The method of claim 3, wherein first treatment regimen comprises administering to the subject, on a continuous basis throughout one or more consecutive treatment periods, about 8 mg of estriol daily.

5. The method of claim 1, wherein the second treatment regimen comprises administering to the subject, on a continuous basis throughout one or more consecutive treatment periods, about 1 mg to about 40 mg of estriol daily.

6. The method of claim 5, wherein the second treatment regimen comprises administering to the subject, on a continuous basis throughout one or more consecutive treatment periods, about 2 mg to about 20 mg of estriol daily.

7. The method of claim 6, wherein second treatment regimen comprises administering to the subject, on a continuous basis throughout one or more consecutive treatment periods, about 12 mg of estriol daily.

8. The method of claim 2, wherein each treatment period of the first treatment regimen and/or second treatment regimen is at least 28 consecutive days, at least 56 consecutive days, least 84 consecutive days, at least 112 consecutive days, at least 4 consecutive weeks, at least 8 consecutive weeks, at least 12 consecutive weeks, at least 16 consecutive weeks, at least one month, at least two consecutive months, at least three consecutive months, or at least four consecutive months.

9. The method of claim 2, wherein the continuous basis is once per day.

10. The method of claim 1, wherein the first treatment regimen and/or second treatment regimen further comprises administering to the subject, for only a portion of each treatment period, a therapeutically effective amount of a progestogen.

11. The method of claim 10, wherein the progestogen is selected from chlormadinone acetate, cyproterone acetate, desogestrel, dienogest, 5α-dihydroprogesterone, drospirenone, ethinodiol acetate, ethynodiol diacetate, etonogestrel, gestodene, 17-hydroxyprogesterone, levonorgestrel, medroxyprogesterone acetate (17α-hydroxy-6α-methylprogesterone acetate), megestrol, megestrol acetate (17α-acetoxy-6-dehydro-6-methylprogesterone), nestorone, nomegestrol acetate, norethindrone, norethindrone acetate, norethynodrel, norgestimate, norgestrel, progesterone, tanaproget, trimegestone, pharmaceutically acceptable salts of any of the foregoing, and any combination thereof.

12. The method of claim 11, wherein the progestogen is norethindrone.

13. The method of claim 12, wherein the progestogen is administered orally in a dose equal or equivalent to about 70 µg to about 7 mg of norethindrone daily.

14. The method of claim 13, wherein the progestogen is administered orally in a dose equal or equivalent to about 700 µg of norethindrone daily.

15. A method for reducing cortical gray matter atrophy in a human subject suffering from multiple sclerosis receiving a first estriol treatment regimen, comprising:
   obtaining a measurement of the serum estriol concentration in the subject; and administering a second estriol treatment regimen to the subject if the serum estriol concentration is less than 6 ng/mL;
   wherein the first treatment regimen comprises:
   administering orally to the subject, on a continuous basis for 84 consecutive days, 8 mg of estriol daily; and
   administering orally to the subject, for 14 consecutive days of the 84 consecutive days, 0.7 mg of norethindrone daily; and
   wherein the daily amount of estriol administered during the second estriol treatment regimen is greater than the daily amount of estriol administered during the first estriol treatment regimen.

16. The method of claim 15, wherein the second treatment regimen comprises:
   administering orally to the subject, on a continuous basis for 84 consecutive days, 12 mg of estriol daily; and
   administering orally to the subject, for 14 consecutive days of the 84 consecutive days, 0.7 mg of norethindrone daily.

17. A method for reducing cortical gray matter atrophy in a subject suffering from multiple sclerosis and receiving a first estriol treatment regimen, comprising:
   obtaining a measurement of the serum estriol concentration in the subject; and administering a second estriol treatment regimen to the subject if the serum estriol concentration is less than 6 ng/mL;
   wherein the second treatment regimen comprises:
   administering orally to the subject, on a continuous basis for 84 consecutive days, 12 mg of estriol daily; and
   wherein administering orally to the subject, for 14 consecutive days of the 84 consecutive days, 0.7 mg of norethindrone daily; and
   the daily amount of estriol administered during the second estriol treatment regimen is greater than the daily amount of estriol administered during the first estriol treatment regimen.

* * * * *